US010828310B2

(12) United States Patent
Bruns et al.

(10) Patent No.: US 10,828,310 B2
(45) Date of Patent: Nov. 10, 2020

(54) REDUCING THE RISK OF CARDIOVASCULAR EVENTS

(71) Applicant: Bayer Pharma Aktiengesellschaft, Berlin (DE)

(72) Inventors: Nancy Cook Bruns, Kassel (DE); Frank Misselwitz, Heidelberg-Neuenheim (DE); John William Andrew Eikelboom, Hamilton (CA); Stuart J. Connolly, Hamilton (CA); Salim Yusuf, Hamilton (CA)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 16/264,032

(22) Filed: Jan. 31, 2019

(65) Prior Publication Data
US 2019/0240231 A1 Aug. 8, 2019

Related U.S. Application Data

(60) Provisional application No. 62/625,646, filed on Feb. 2, 2018.

(51) Int. Cl.
| A61K 31/5377 | (2006.01) |
| A61P 9/10 | (2006.01) |
| A61K 31/616 | (2006.01) |

(52) U.S. Cl.
CPC ........ *A61K 31/5377* (2013.01); *A61K 31/616* (2013.01); *A61P 9/10* (2018.01)

(58) Field of Classification Search
USPC ...................................................... 514/161
See application file for complete search history.

(56) References Cited

U.S. PATENT DOCUMENTS

| 7,157,456 | B2 | 1/2007 | Straub et al. | |
| 9,402,851 | B2 | 8/2016 | Benke | |
| 2003/0191109 | A1* | 10/2003 | Kahn | A61K 31/4035 514/211.05 |
| 2010/0120718 | A1* | 5/2010 | Perzborn | A61K 31/4365 514/81 |
| 2013/0303462 | A1* | 11/2013 | Klein | C07D 473/06 514/20.5 |

FOREIGN PATENT DOCUMENTS

| WO | 0147919 | 7/2001 |
| WO | 03000256 | 1/2003 |
| WO | 2017180683 | 10/2017 |

OTHER PUBLICATIONS

Anand et. al. (The Lancet (published online on Nov. 10, 2017), (Year: 2017).*
Reagan-Shaw et. al (FASEB Journal (2007) 22:659-661). (Year: 2007).*
Anand et. al. (J. Am. Coll. Cardiol. (2003) 41:62S-69S). (Year: 2003).*
Ringwala et. al. (J. Thromb. Thrombolysis (2012) 34:291-296). (Year: 2012).*
Study Protocol NCT01776424 (Aug. 19, 2015). (Year: 2015).*
The Warfarin Antiplatelet Vascular Evaluation Trial Investigators, Oral Anticoagulant and Antiplatelet Therapy and Peripheral Arterial Disease; N Eng J Med 2007; 357:217-27.
The Dutch Bypass Oral Anticoagulants or Aspirin Study Group, Efficacy of oral anticoagulants compared with aspirin after infrainguninal bypass surgery; Lancet 2000; 355: 346-51.
Anand S. et al., Rivaroxaban with or without aspirin in patients with stable peripheral or carotid artery disease: an international, randomised, double-blind, placebo-controlled trial; Lancet 2017; 391: 219-229.
Anand, "Oral anticoagulants in patients with coronary artery disease," J Am Coll Cardiol 2003:41:Suppl S:62S-69S.
Caprie Steering Committee, A randomized, blinded, trial of clopidogrel versus aspirin in patients at risk of ischaemic avents (Caprie), Lancet 1996;348:1329-39.
Bhatt et al., "Clopidogrel and aspirin versus aspirin alone for the prevention of atherothrombotic events," N Engl J Med 2006;354:1706-17.
Bonaca et al., "Long-term use of ticagrelor in patients with prior myocardial infarction," N Engl J Med 2015;372:1791-(800).
Hiatt et al., "Ticagrelor versus clopidogrel in symptomatic peripheral artery disease," N Engl J Med 2017;376:32-40.
Morrow et al., "Vorapaxar in the secondary prevention of atherothrombotic events," N Engl J Med 2012;366:1404-13.
Mega et al., "Rivaroxaban in patients with a recent acute coronary syndrome," N Engl J Med 2012;366:9-19.
European Medicines Agency, "Assessment report: Xarelto", Mar. 21, 2013, pp. 1-75.
BOSCH et al., "Rationale, Design and Baseline Characteristics of Participants in the Cardiovascular Outcomes for People Using Anticoagulation Strategies (COMPASS) Trial," Canadian Journal of Cardiology, 33, Jun. 2017, pp. 1027-1035.
Sanchis-Gomar et al., "Epidemiology of Coronary Heart Disease and Acute Coronary Syndrome," Annuals of Translational Medicine,(13), Jul. 2016, 12 pages.
U.S. National Library of Medicine, "Rivaroxaban for the Prevention of Major Cardiovascular Events in Coronary or Peripheral Artery Disease," ClinicalTrials.gov Archives, http://clinicaltrials.gov/ct2/history/NCT01776424?V_49=View#StudyPageTop, (accessed May 9, 2019), 33 pages.
Eikelboom et al., "Rivaroxaban with or without aspirin in stable cardiovascular disease," n Engl J Med 2017;377;1319-30.
Lancet; Rivaroxaban with or without aspirin in patients with stable peripheral or carotid artery disease: an international, randomised, double-blind, placebo-controlled trial; published online at S0140-6736(17)32409-1 on Nov. 10, 2017)).

(Continued)

*Primary Examiner* — Marcos L Sznaidman
(74) *Attorney, Agent, or Firm* — Quarles & Brady LLP

(57) ABSTRACT

Combination therapy with rivaroxaban and aspirin successfully reduces the risk of cardiovascular events in patients who have coronary artery disease and/or peripheral artery disease.

8 Claims, 13 Drawing Sheets

(56) References Cited

OTHER PUBLICATIONS

Connolly et al., 2017. Rivaroxaban With or Without Aspirin in Patients with Stable Coronary Artery Disease: an International, Randomised, Double-blind, Placebo-controlled Trial. The Lancet, 391(10117), 205-218. https://doi.org/10.1016/S0140-6736(17)32458-3.

* cited by examiner

| TABLE 1. BASELINE CHARACTERISTICS OF THE PARTICIPANTS | | | |
|---|---|---|---|
| CHARACTERISTIC | RIVAROXABAN PLUS ASPIRIN (N=9152) | RIVAROXABAN ALONE (N=9117) | ASPIRIN ALONE (N=9126) |
| AGE-YR | 68.3±7.9 | 68.2±7.9 | 68.2±8.0 |
| FEMALE SEX - NO. (%) | 2059 (22.5) | 1972 (21.6) | 1989 (21.8) |
| BODY-MASS INDEX† | 28.3±4.8 | 28.3±4.6 | 28.3±4.7 |
| BLOOD PRESSURE - mmHg | | | |
| SYSTOLIC | 136±17 | 136±18 | 136±18 |
| DIASTOLIC | 77±10 | 78±10 | 78±10 |
| CHOLESTEROL - mmol/liter | 4.2±1.1 | 4.2±1.1 | 4.2±1.1 |
| TOBACCO USE - NO. (%) | 1944 (21.2) | 1951 (21.4) | 1972 (21.6) |
| HYPERTENSION - NO. (%) | 6907 (75.5) | 6848 (75.1) | 6877 (75.4) |
| DIABETES - NO. (%) | 3448 (37.7) | 3419 (37.5) | 3474 (38.1) |
| PREVIOUS STROKE - NO. (%) | 351 (3.8) | 346 (3.8) | 335 (3.7) |
| PREVIOUS MYOCARDIAL INFARCTION - NO. (%) | 5654 (61.8) | 5653 (62.0) | 5721 (62.7) |
| HEART FAILURE - NO. (%) | 1963 (21.4) | 1960 (21.5) | 1979 (21.7) |
| CORONARY ARTERY DISEASE - NO. (%) ‡ | 8313 (90.8) | 8250 (90.5) | 8261 (90.5) |
| PERIPHERAL ARTERIAL DISEASE - NO. (%)δ | 2492 (27.2) | 2474 (27.1) | 2504 (27.4) |
| ESTIMATED GFR - NO. (%)¶ | | | |
| <30ml/min | 77 (0.8) | 80 (0.9) | 86 (0.9) |
| 30 TO <60ml/min | 1977 (21.6) | 2028 (22.2) | 2028 (22.2) |
| ≥60 ml/min | 7094 (77.5) | 7005 (76.8) | 7012 (76.8) |
| RACE - NO. (%) ∥ | | | |
| WHITE | 5673 (62.0) | 5672 (62.2) | 5682 (62.3) |
| BLACK | 76 (0.8) | 94 (1.0) | 92 (1.0) |

FIG. 1A

| CHARACTERISTIC | RIVAROXABAN PLUS ASPIRIN (N=9152) | RIVAROXABAN ALONE (N=9117) | ASPIRIN ALONE (N=9126) |
|---|---|---|---|
| ASIAN | 1451 (15.9) | 1421 (15.6) | 1397 (15.3) |
| OTHER | 1952 (21.3) | 1930 (21.2) | 1955 (21.4) |
| GEOGRAPHIC REGION - NO. (%) | | | |
| NORTH AMERICA | 1304 (14.2) | 1305 (14.3) | 1309 (14.3) |
| SOUTH AMERICA | 2054 (22.4) | 2036 (22.3) | 2054 (22.5) |
| WESTERN EUROPE, ISRAEL, AUSTRALIA OR SOUTH AFRICA | 2855 (31.2) | 2855 (31.2) | 2855 (31.3) |
| EASTERN EUROPE | 1607 (17.6) | 1612 (17.7) | 1604 (17.6) |
| ASIA-PACIFIC | 1332 (14.6) | 1319 (14.5) | 1304 (14.3) |
| MEDICATION - NO. (%) | | | |
| ACE INHIBITOR OR ARB | 6475 (70.7) | 6581 (72.2) | 6462 (70.8) |
| CALCIUM-CHANNEL BLOCKER | 2413 (26.4) | 2374 (26.0) | 2482 (27.2) |
| DIURETIC | 2727 (29.8) | 2666 (29.2) | 2746 (30.1) |
| BETA-BLOCKER | 6389 (69.8) | 6401 (70.2) | 6394 (70.1) |
| LIPID-LOWERING AGENT | 8239 (90.8) | 8204 (90.0) | 8158 (89.4) |
| NSAID | 531 (5.8) | 466 (5.1) | 473 (5.2) |
| NONTRIAL PPI | 3268 (35.7) | 3266 (35.8) | 3264 (35.8) |

FIG. 1B

TABLE 2. EFFICACY OUTCOMES*

| OUTCOME | RIVAROXABAN PLUS ASPIRIN (N=9152) | RIVAROXABAN ALONE (N=9117) | ASPIRIN ALONE (N=9126) | RIVAROXABAN PLUS ASPIRIN VS. ASPIRIN ALONE | | RIVAROXABAN ALONE VS. ASPIRIN ALONE | |
|---|---|---|---|---|---|---|---|
| | | | | Hazard Ratio (95% CI) | P Value | Hazard Ratio (95% CI) | P Value |
| | number (percent) | | | | | | |
| PRIMARY OUTCOME: CV DEATH, STROKE, OR MYOCARDIAL INFARCTION† | 379 (4.1) | 448 (4.9) | 496 (5.4) | 0.76 (0.66-0.86) | <0.001 | 0.90 (0.79-1.03) | 0.12 |
| SECONDARY OUTCOMES | | | | | | | |
| ISCHEMIC STROKE, MYOCARDIAL INFARCTION, ALI, OR DEATH FROM CHD | 329 (3.6) | 397 (4.4) | 450 (4.9) | 0.72 (0.63-0.83) | <0.001 | 0.88 (0.77-1.01) | 0.06 |
| ISCHEMIC STROKE, MYOCARDIAL INFARCTION, ALI, OR CV DEATH | 389 (4.3) | 453 (5.0) | 516 (5.7) | 0.74 (0.65-0.85) | <0.001 | 0.88 (0.77-0.99) | 0.04 |
| DEATH FROM ANY CAUSE | 313 (3.4) | 366 (4.0) | 378 (4.1) | 0.82 (0.71-0.96) | 0.01 | 0.97 (0.84-1.12) | 0.67 |

FIG. 2A

| OUTCOME | RIVAROXABAN PLUS ASPIRIN (N=9152) | RIVAROXABAN ALONE (N=9117) | ASPIRIN ALONE (N=9126) | RIVAROXABAN PLUS ASPIRIN VS. ASPIRIN ALONE | | RIVAROXABAN ALONE VS. ASPIRIN ALONE | |
|---|---|---|---|---|---|---|---|
| | | | | Hazard Ratio (95% CI) | P Value | Hazard Ratio (95% CI) | P Value |
| | number (percent) | | | | | | |
| OTHER OUTCOMES§ | | | | | | | |
| CV DEATH | 160 (1.7) | 195 (2.1) | 203 (2.2) | 0.78 (0.64-0.96) | 0.02 | 0.96 (0.79-1.17) | 0.69 |
| NON-CV DEATH | 153 (1.7) | 171 (1.9) | 175 (1.9) | 0.87 (0.70-1.08) | 0.20 | 0.98 (0.79-1.21) | 0.84 |
| DEATH FROM CHD | 86 (0.9) | 128 (1.4) | 117 (1.3) | 0.73 (0.55-0.96) | 0.03 | 1.09 (0.95-1.41) | 0.48 |
| STROKE | 83 (0.9) | 117 (1.3) | 142 (1.6) | 0.58 (0.44-0.76) | <0.001 | 0.82 (0.65-1.05) | 0.12 |
| ISCHEMIC OR UNCERTAIN TYPE | 68 (0.7) | 91 (1.0) | 132 (1.4) | 0.51 (0.38-0.68) | <0.001 | 0.69 (0.53-0.90) | 0.006 |
| HEMORRHAGIC | 15 (0.2) | 27 (0.3) | 10 (0.1) | 1.49 (0.67-3.31) | 0.33 | 2.70 (1.31-5.58) | 0.005 |
| MYOCARDIAL INFARCTION | 178 (1.9) | 182 (2.0) | 205 (2.2) | 0.86 (0.70-1.05) | 0.14 | 0.89 (0.73-1.08) | 0.24 |
| HEART FAILURE | 197 (2.2) | 191 (2.1) | 192 (2.1) | 1.02 (0.84-1.24) | 0.84 | 0.99 (0.81-1.21) | 0.95 |
| VENOUS THROMBOEMBOLISM | 25 (0.3) | 36 (0.4) | 41 (0.4) | 0.61 (0.37-1.00) | 0.05 | 0.88 (0.56-1.38) | 0.58 |
| HOSPITALIZATION | | | | | | | |
| FOR CV CAUSES | 1303 (14.2) | 1317 (14.4) | 1394 (15.3) | 0.92 (0.86-1.00) | 0.04 | 0.94 (0.87-1.01) | 0.11 |
| FOR NON-CV CAUSES | 1701 (18.6) | 1649 (18.1) | 1624 (17.8) | 1.05 (0.98-1.13) | 0.14 | 1.02 (0.95-1.09) | 0.54 |

FIG. 2B

TABLE 3. BLEEDING EVENTS AND NET CLINICAL BENEFIT*

| OUTCOME | RIVAROXABAN PLUS ASPIRIN (N=9152) | RIVAROXABAN ALONE (N=9117) | ASPIRIN ALONE (N=9126) | RIVAROXABAN PLUS ASPIRIN VS. ASPIRIN ALONE | | RIVAROXABAN ALONE VS. ASPIRIN ALONE | |
|---|---|---|---|---|---|---|---|
| | | | | Hazard Ratio (95% CI) | P Value | Hazard Ratio (95% CI) | P Value |
| | number (percent) | | | | | | |
| MAJOR AND MINOR BLEEDING | | | | | | | |
| MAJOR BLEEDING | 288 (3.1) | 255 (2.8) | 170 (1.9) | 1.70 (1.40-2.05) | <0.001 | 1.51 (1.25-1.84) | <0.001 |
| FATAL BLEEDING † | 15 (0.2) | 14 (0.2) | 10 (0.1) | 1.49 (0.67-3.33) | 0.32 | 1.40 (0.62-3.15) | 0.41 |
| NONFATAL SYMPTOMATIC ICH † | 21 (0.2) | 32 (0.4) | 19 (0.2) | 1.10 (0.59-2.04) | 0.77 | 1.69 (0.96-2.98) | 0.07 |
| NONFATAL, NON-ICH, SYMPTOMATIC BLEEDING INTO CRITICAL ORGAN † | 42 (0.5) | 45 (0.5) | 29 (0.3) | 1.43 (0.89-2.29) | 0.14 | 1.57 (0.98-2.50) | 0.06 |
| OTHER MAJOR BLEEDING † | 210 (2.3) | 164 (1.8) | 112 (1.2) | 1.88 (1.49-2.36) | <0.001 | 1.47 (1.16-1.87) | 0.001 |
| FATAL BLEEDING OR SYMPTOMATIC ICH | 36 (0.4) | 46 (0.5) | 29 (0.3) | 1.23 (0.76-2.01) | 0.40 | 1.59 (1.00-2.53) | 0.05 |
| FATAL BLEEDING OR SYMPTOMATIC BLEEDING INTO CRITICAL ORGAN | 78 (0.9) | 91 (1.0) | 58 (0.6) | 1.34 (0.95-1.88) | 0.09 | 1.58 (1.13-2.19) | 0.006 |
| MAJOR BLEEDING ACCORDING TO ISTH CRITERIA | 206 (2.3) | 175 (1.9) | 116 (1.3) | 1.78 (1.41-2.23) | <0.001 | 1.52 (1.20-1.92) | <0.001 |
| TRANSFUSION WITHIN 48HR AFTER BLEEDING | 87 (1.0) | 66 (0.7) | 44 (0.5) | 1.97 (1.37-2.83) | <0.001 | 1.50 (1.03-2.20) | 0.03 |
| MINOR BLEEDING | 838 (9.2) | 741 (8.1) | 503 (5.5) | 1.70 (1.52-1.90) | <0.001 | 1.50 (1.34-1.68) | <0.001 |

FIG. 5A

| OUTCOME | RIVAROXABAN PLUS ASPIRIN (N=9152) | RIVAROXABAN ALONE (N=9117) | ASPIRIN ALONE (N=9126) | RIVAROXABAN PLUS ASPIRIN VS. ASPIRIN ALONE | | RIVAROXABAN ALONE VS. ASPIRIN ALONE | |
|---|---|---|---|---|---|---|---|
| | | | | Hazard Ratio (95% CI) | P Value | Hazard Ratio (95% CI) | P Value |
| | number (percent) | | | | | | |
| SITE OF MAJOR BLEEDING | | | | | | | |
| GASTROINTESTINAL | 140 (1.5) | 91 (1.0) | 65 (0.7) | 2.15 (1.60-2.89) | <0.001 | 1.40 (1.02-1.93) | 0.04 |
| INTRACRANIAL | 28 (0.3) | 43 (0.5) | 24 (0.3) | 1.16 (0.67-2.00) | 0.60 | 1.80 (1.09-2.96) | 0.02 |
| SKIN OR INJECTION SITE | 28 (0.3) | 28 (0.3) | 12 (0.1) | 2.31 (1.18-4.54) | 0.01 | 2.34 (1.19-4.60) | 0.01 |
| URINARY | 13 (0.1) | 30 (0.3) | 21 (0.2) | 0.61 (0.31-1.23) | 0.16 | 1.43 (0.82-2.50) | 0.20 |
| NET-CLINICAL-BENEFIT OUTCOME: CV DEATH, STROKE, MYOCARDIAL INFARCTION, FATAL BLEEDING, OR SYMPTOMATIC BLEEDING INTO CRITICAL ORGAN | 431 (4.7) | 504 (5.5) | 534 (5.9) | 0.80 (0.70-0.91) | <0.001 | 0.94 (0.84-1.07) | 0.36 |

FIG. 5B

SUBGROUP ANALYSES FOR THE PRIMARY OUTCOME FOR THE COMPARISON OF RIVAROXABAN PLUS ASPIRIN WITH ASPIRIN ALONE.

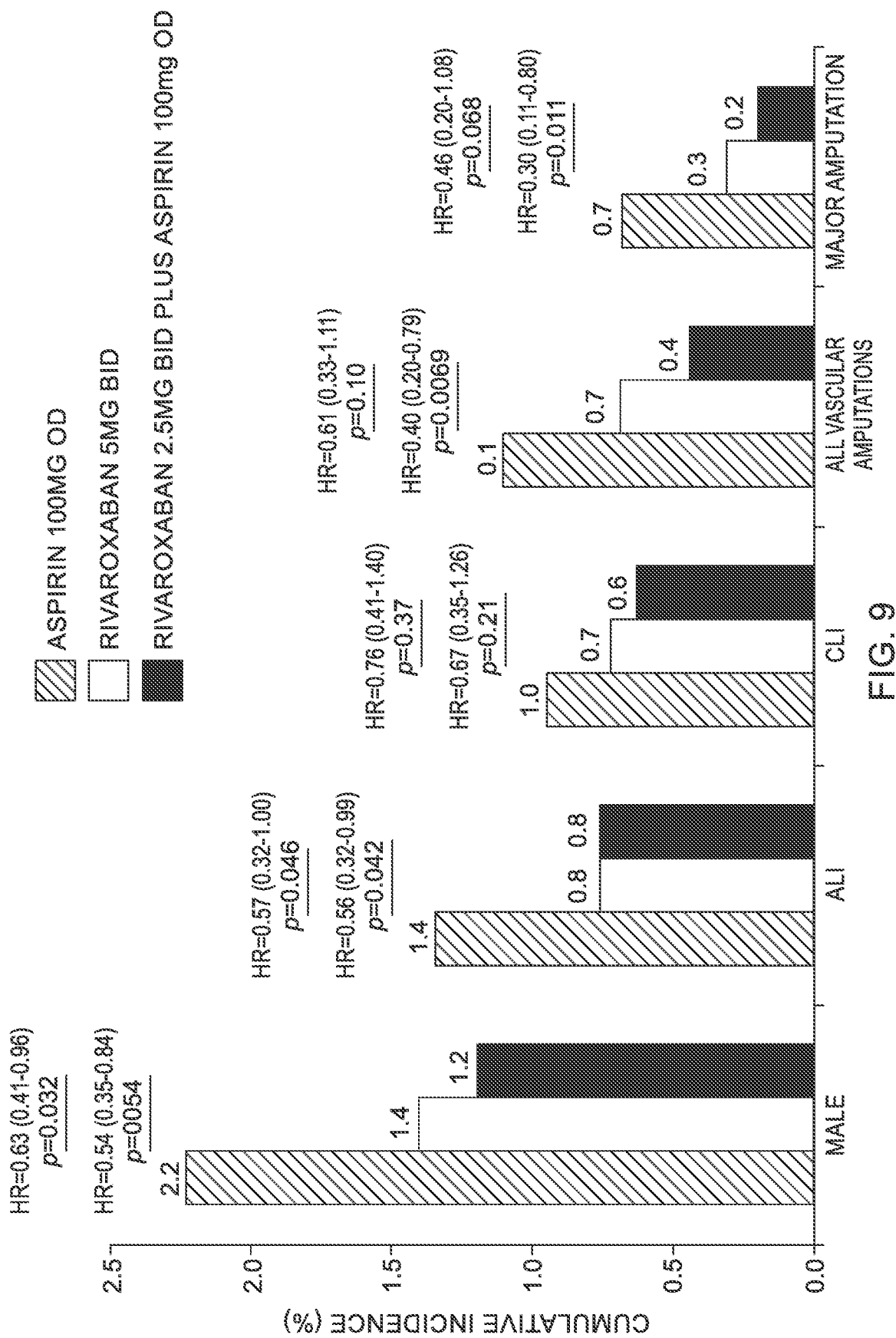

REDUCING THE RISK OF CARDIOVASCULAR EVENTS

CROSS-REFERENCE TO RELATED APPLICATION

This invention claims priority to U.S. Provisional Application Ser. No. 62/625,646, entitled "REDUCING THE RISK OF CARDIOVASCULAR EVENTS," filed Feb. 2, 2018, the contents of which are hereby incorporated by reference in its entirety.

FIELD OF THE INVENTION

The present invention concerns medical therapy to treat or prevent cardiovascular events in patients with atherosclerotic vascular disease, coronary artery disease and/or peripheral arterial disease.

BACKGROUND OF THE INVENTION

Rivaroxaban is a medication used for the treatment and prevention of thromboembolic disorders. Rivaroxaban has the chemical name 5-chloro-N-({(5S)-2-oxo-3-[4-(3-oxo-4-morpholinyl)phenyl]-1,3-oxazolidin-5-yl}methyl)-2-thiophenecarboxamide, and has the chemical structure of the formula (I):

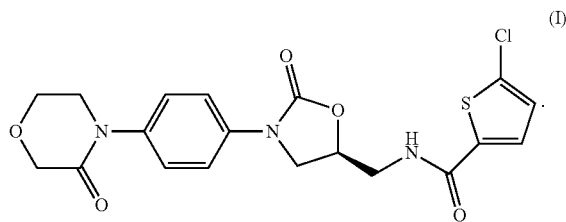 [SMILES: O=C(NC[C@H]1CN(c2ccc(N3CCOCC3=O)cc2)C(=O)O1)c1ccc(Cl)s1]

Rivaroxaban acts as a selective inhibitor of coagulation factor Xa (FXa) and as an anticoagulant (WO 01/47919). Combinations of FXa inhibitors with platelet aggregation inhibitors, anticoagulants, fibrinolytics, lipid-lowering agents, coronary therapeutic agents and/or vasodilators are described in WO 03/000256. Combinations of the compound of formula (I) with acetylsalicylic acid and clopidogrel are disclosed in US Pat. App. Pub. 2010/0120718 A1.

Coronary artery disease ("CAD"), also called coronary heart disease, is the most common type of heart disease. It occurs when plaque builds up in the heart's arteries, a condition called atherosclerosis. As plaque builds up, the arteries narrow, making it more difficult for blood to flow to the heart. If blood flow becomes reduced or blocked, angina (chest pain) or a heart attack may occur. Over time, coronary artery disease can also lead to heart failure and arrhythmias. Peripheral artery disease ("PAD") occurs when narrow arteries reduce blood flow to the limbs and the head, such as narrowed arteries to the legs, feet and/or head. Symptoms can include pain in the legs or buttocks when exercising that goes away when the activity is stopped, or abrupt closure of the vessels in the neck leading to brain damage (stroke). PAD is a progressive vascular disease that may lead to atherothrombosis, acute or chronic limb ischemia, amputation, and stroke. Both PAD and CAD are caused by atherosclerosis that narrows and blocks arteries in various critical regions of the body.

Patients with PAD or CAD are at high risk for major adverse cardiovascular events of myocardial infarction, stroke, and cardiovascular death. Anticoagulant therapies until the present invention have not been shown to the satisfaction of governmental health authorities to be superior to antiplatelet therapy in PAD and have been rejected as having unacceptably high rates of major bleeding (Warfarin Antiplatelet Vascular Evaluation Trial Investigators, Anand S et al., N Eng J Med 2007; 357:217-27). Specifically, high and moderate intensity warfarin used with aspirin does not reduce major adverse cardiovascular events but does increase the risk of life-threatening bleeding, including intracranial hemorrhage (The Dutch Bypass Oral Anticoagulants or Aspirin Study Group, Lancet 2000; 355: 346-51). The mainstay of treatment for patients with PAD includes use of a single antiplatelet agent daily to prevent major adverse cardiovascular events. Other antithrombotic regimens have been tested in PAD patients including vitamin K antagonists and newer antiplatelet agents such as P2Y12 antagonists used alone or in combination with aspirin, but none have been shown to be superior to antiplatelet therapy alone (Anand S. et al., Lancet 2017; 391: 219-229).

Antiplatelet therapy is frequently used in patients with CAD. For example, aspirin alone, or aspirin in combination with an antiplatelet agent from the class known as P2Y12 inhibitors such as clopidogrel are used in CAD patients. Despite the availability of these therapies, there is still a need for new approaches to improve health outcomes in CAD and PAD patients.

Various antithrombotic regimens have been tested as alternatives to aspirin for long-term cardiovascular prevention. Trials of vitamin K antagonists involving patients with stable cardiovascular disease showed a reduction in the risk of subsequent cardiovascular events (Anand, "Oral anticoagulants in patients with coronary artery disease," J Am Coll Cardiol 2003:41:Suppl S:62S-69S). However, there was no benefit in patients with peripheral arterial disease (The Warfarin Antiplatelet Vascular Evaluation Trial Investigators, "Oral anti-coagulant and antiplatelet therapy and peripheral arterial disease," N Engl J Med 2007; 357:217-27), and there was a significant increase in bleeding, including intracranial bleeding (Anand, J Am Coll Cardiol and The Warfarin Antiplatelet Vascular Evaluation Trial Investigators, supra). Among patients with stable cardiovascular disease, those who received clopidogrel had a lower risk of major adverse cardiovascular events than those who received aspirin, but there was no significant difference in the risk of cardiovascular death or death from any cause (CAPRIE Steering Committee, "A randomized, blinded, trial of clopidogrel versus aspirin in patients at risk of ischaemic events (CAPRIE), Lancet 1996; 348:1329-39). Among patients with symptomatic stable cardiovascular disease or multiple risk factors, the combination of clopidogrel and aspirin did not result in a significantly lower rate of major adverse cardiovascular events or death from any cause than aspirin alone (Bhatt, "Clopidogrel and aspirin versus aspirin alone for the prevention of atherothrombotic events," N Engl J Med 2006; 354:1706-17). Among patients who had had myocardial infarction 1 to 3 years previously, the combination of ticagrelor and aspirin resulted in a lower rate of major adverse cardiovascular events and a higher rate of major bleeding than aspirin alone, and there was no significant between-group difference in mortality (Bonaca, "Long-term use of ticagrelor in patients with prior myocardial infarction," N Engl J Med 2015; 372:1791-800). Among patients with stable peripheral arterial disease, ticagrelor did not result in a significantly lower rate of major adverse cardiovascular events than clopidogrel (Hiatt, "Ticagrelor versus clopidogrel in symptomatic peripheral artery disease," N Engl J Med 2017; 376:32-40). Among patients with stable cardiovascular disease who were receiving single or dual antiplatelet therapy, vorapaxar, a PAR-1 receptor antagonist, resulted in a lower rate of major adverse cardiovascular events and a higher rate of moderate or severe bleeding than placebo, with no significant between-group difference in mortality (Morrow, "Vorapaxar in the secondary prevention of atherothrombotic events," N Engl J Med 2012; 366:1404-13).

The potential benefit of rivaroxaban in patients with cardiovascular disease was evaluated in the Anti-Xa Therapy to Lower Cardiovascular Events in Addition to Standard Therapy in Subjects with Acute Coronary Syndrome 2—Thrombolysis in Myocardial Infarction 51 (ATLAS ACS 2-TIMI 51) trial and the dose-finding trial associated with it, ATLAS ACS-TIMI 46. The ATLAS ACS 2-TIMI 51 trial tested rivaroxaban on a background of single or dual antiplatelet therapy in patients with a recent acute coronary syndrome. Rivaroxaban at a dose of 2.5 mg twice daily or 5 mg twice daily resulted in a lower rate of major adverse cardiovascular events than placebo, and the dose of 2.5 mg twice daily resulted in lower mortality (Mega, "Rivaroxaban in patients with a recent acute coronary syndrome," N Engl J Med 2012; 366:9-19).

The findings presented herein were obtained from the phase III COMPASS trial evaluating the efficacy and safety of rivaroxaban (Xarelto®) for the prevention of major adverse cardiac events including cardiovascular death, myocardial infarction and stroke in patients with CAD or PAD, and are reported in Eikelboom et al., "Rivaroxaban with or without aspirin in stable cardiovascular disease," N Engl J Med 2017; 377; 1319-30. The mean duration of rivaroxaban treatment in the ATLAS ACS 2-TIMI 51 trial was 13.3 months, whereas persons enrolled in the COMPASS trial who had a history of myocardial infarction were enrolled a mean of 7.1 years after the acute event and continued to receive treatment for a mean of 23 months.

WO2017180683 A2 to Adams Pharmaceuticals discloses methods of preventing atherosclerosis by administering an inhibitor of factor Xa, such as rivaroxaban, apixaban, betrixaban, edoxaban, and otamixaban.

SUMMARY

The invention concerns the discovery that combination therapy of rivaroxaban and aspirin administered to patients with stable atherosclerotic vascular disease, including coronary artery disease and/or peripheral artery disease, shows efficacy in reducing the risk of myocardial infarction, stroke, and/or cardiovascular death. Furthermore, this combination therapy does not result in unacceptable bleeding, such as an unacceptably high risk of fatal bleeding or bleeding in critical organs.

In one embodiment, the invention is a method of reducing the risk of myocardial infarction, stroke or cardiovascular death in a human patient with coronary artery disease and/or peripheral artery disease, comprising administering to the human patient rivaroxaban and aspirin in amounts that are clinically proven effective in reducing the risk of myocardial infarction, stroke or cardiovascular death in a human patient with coronary artery disease and/or peripheral arterial disease, wherein rivaroxaban is administered in an amount of 2.5 mg twice daily and aspirin is administered in an amount of 75-100 mg daily, or in an amount of 75 mg, 81 mg or 100 mg daily. In another embodiment, the invention is a method of reducing the risk of myocardial infarction, stroke or cardiovascular death in a human patient with coronary artery disease and/or peripheral artery disease, the method comprising administering to the human patient a product comprising rivaroxaban and aspirin in amounts that are clinically proven effective in reducing the risk of myocardial infarction, stroke or cardiovascular death in a human patient with coronary artery disease and/or peripheral arterial disease, wherein rivaroxaban is administered in an amount of 2.5 mg twice daily and aspirin is administered in an amount of 75-100 mg daily. The invention also concerns an effective pharmaceutical product for reducing the risk of myocardial infarction, stroke or cardiovascular death in a human patient with coronary artery disease and/or peripheral artery disease, wherein the pharmaceutical product comprises 2.5 mg rivaroxaban and 75-100 mg, 75 mg, 81 mg or 100 mg aspirin. In another embodiment, the invention also concerns an effective pharmaceutical product for reducing the risk of myocardial infarction, stroke or cardiovascular death in a human patient with coronary artery disease and/or peripheral artery disease, wherein the pharmaceutical product comprises 2.5 mg rivaroxaban and 35-38 mg, 39-41 mg, or 49-51 mg aspirin.

In another embodiment, the invention is a method of reducing the risk of major adverse limb events (MALE), including without limitation acute limb ischemia, in a human patient with peripheral artery disease, comprising administering to the human patient rivaroxaban and aspirin in amounts that are clinically proven effective in reducing the risk of risk of major adverse limb events such as acute limb ischemia in a human patient with peripheral arterial disease, wherein rivaroxaban is administered in an amount of 2.5 mg twice daily and aspirin is administered in an amount of 75-100 mg daily, or in an amount of 75 mg, 81 mg or 100 mg daily. In another embodiment, the invention is a method of reducing the risk of major adverse limb events, such as without limitation acute limb ischemia, in a human patient with peripheral artery disease, the method comprising administering to the human patient a product comprising rivaroxaban and aspirin in amounts that are clinically proven effective in reducing the risk of major adverse limb events, such as without limitation acute limb ischemia, in a human patient with peripheral arterial disease, wherein rivaroxaban is administered in an amount of 2.5 mg twice daily and aspirin is administered in an amount of 75-100 mg daily. The invention also concerns an effective pharmaceutical product for reducing the risk of major adverse limb events, such as without limitation acute limb ischemia, in a human patient with peripheral artery disease, wherein the pharmaceutical product comprises 2.5 mg rivaroxaban and 75-100 mg, 75 mg, 81 mg or 100 mg aspirin. In another embodiment, the invention also concerns an effective pharmaceutical product for reducing the risk of major adverse limb events, such as without limitation acute limb ischemia, in a human patient with peripheral artery disease, wherein the pharmaceutical product comprises 2.5 mg rivaroxaban and 35-38 mg, 39-41 mg, or 49-51 mg aspirin.

Another embodiment of the invention is a method of reducing the risk of myocardial infarction, stroke or cardiovascular death in a population of human patients with coronary artery disease and/or peripheral artery disease, comprising administering to each human patient in the population rivaroxaban and aspirin in amounts that are clinically proven effective in reducing the risk of myocardial infarction, stroke or cardiovascular death in a human patient with coronary artery disease and/or peripheral arterial disease, wherein rivaroxaban is administered in an amount of 2.5 mg twice daily and aspirin is administered in an amount of 75-100 mg daily, and wherein the hazard ratio for myocardial infarction, stroke, or cardiovascular death with the administration of rivaroxaban and aspirin compared to aspirin alone is 0.70-0.80 with a 95% confidence interval of at least 0.56 to 0.96, preferably 0.76, and, in certain embodiments, the method additionally has a hazard ratio for major bleeding events with the administration of rivaroxaban and aspirin compared to aspirin alone is 1.60-1.90, preferably 1.84, with a 95% confidence interval of at least 1.35 to 2.15, preferably 1.50 to 2.26, wherein major bleeding events are defined herein using a modified ISTH standard.

Another embodiment of the invention is a method of reducing the risk of stroke, myocardial infarction, or cardiovascular death, in a population of human patients with peripheral artery disease, comprising administering to each human patient in the population rivaroxaban and aspirin in amounts that are clinically proven effective in reducing the risk of stroke, myocardial infarction, or cardiovascular death, in a human patient with peripheral arterial disease, wherein rivaroxaban is administered in an amount of 2.5 mg twice daily and aspirin is administered in an amount of 75-100 mg daily, and wherein the hazard ratio for stroke, myocardial infarction, or cardiovascular death with the administration of rivaroxaban and aspirin compared to aspirin alone is 0.50-0.60, preferably 0.72, with a 95% confidence interval of at least 0.30-1.10, preferably 0.57-0.90. Another embodiment of the invention is a method of reducing the risk of acute limb ischemia in a human patient with peripheral artery disease, comprising administering to the human patient rivaroxaban and aspirin in amounts that are clinically proven effective in reducing the risk of acute limb ischemia in patients with peripheral artery disease, wherein rivaroxaban is administered in an amount of 2.5 mg twice daily and aspirin is administered in an amount of 75-100 mg daily, and wherein the hazard ratio for acute limb ischemia with the administration of rivaroxaban and aspirin compared to aspirin alone is 0.45-0.65, preferably 0.56, with a 95% confidence interval of at least 0.25-1.10, preferably 0.32-0.99.

Another embodiment of the invention is a method of reducing the risk of myocardial infarction, stroke or cardiovascular death in a population of human patients with coronary artery disease and/or peripheral artery disease, comprising administering to each human patient in the population rivaroxaban and aspirin in amounts that are clinically proven effective in reducing the risk of myocardial infarction, stroke or cardiovascular death in a human patient with coronary artery disease and/or peripheral arterial disease, wherein rivaroxaban is administered in an amount of 2.5 mg twice daily and aspirin is administered in an amount of 75-100 mg daily, and wherein the composite outcome of net clinical benefit with the administration of rivaroxaban and aspirin compared to aspirin alone has a hazard ratio of 0.70-0.90 with a 95% confidence interval of at least 0.56 to 0.96, preferably a hazard ratio of 0.80 with a confidence interval of 0.70 to 0.91, wherein the composite outcome of net clinical benefit consists of cardiovascular death, myocardial infarction, stroke, and fatal or symptomatic critical-organ bleeding events.

Another embodiment of the invention is a method of reducing the risk of stroke, myocardial infarction, or cardiovascular death, in a population of human patients with peripheral artery disease, comprising administering to each human patient in the population rivaroxaban and aspirin in amounts that are clinically proven effective in reducing the risk of stroke, myocardial infarction, or cardiovascular death, in a human patient with peripheral arterial disease, wherein rivaroxaban is administered in an amount of 2.5 mg twice daily and aspirin is administered in an amount of 75-100 mg daily, and wherein the composite outcome of net clinical benefit with the administration of rivaroxaban and aspirin compared to aspirin alone has a hazard ratio of 0.60-0.80 with a 95% confidence interval of at least 0.50 to 0.99, preferably a hazard ratio of 0.75 with a confidence interval of 0.60 to 0.94, wherein the composite outcome of net clinical benefit consists of cardiovascular death, myocardial infarction, stroke, and fatal or symptomatic critical-organ bleeding.

BRIEF DESCRIPTION OF THE DRAWING FIGURES

FIG. 1A and FIG. 1B together are Table 1, which shows the baseline characteristics of the COMPASS clinical study participants. The legend for FIGS. 1A and 1B is as follows:

* Plus-minus values are means±SD. There were no significant differences among the three randomized groups. Participants in the rivaroxaban-plus-aspirin group received 2.5 mg of rivaroxaban twice daily and 100 mg of aspirin once daily. Participants in the rivaroxaban-alone group received 5 mg of rivaroxaban twice daily and an aspirin-matched placebo once daily. Participants in the aspirin-alone group received 100 mg of aspirin once daily and a rivaroxaban-matched placebo twice daily. To convert cholesterol values to milligrams per deciliter, divide by 0.02586. ACE denotes angiotensin-converting enzyme, ARB angiotensin-receptor blocker, GFR glomerular filtration rate, NSAID nonsteroidal anti-inflammatory drug, and PPI proton-pump inhibitor.

† The body-mass index is the weight in kilograms divided by the square of the height in meters.

‡ Shown are patients with a history of coronary artery disease irrespective of whether it met the inclusion criteria for the trial.

δ Shown are patients with a history of peripheral arterial disease irrespective of whether it met the inclusion criteria for the trial.

¶ The GFR was calculated by means of the Chronic Kidney Disease Epidemiology Collaboration formula. Data on GFR were missing for four patients in the rivaroxaban-plus-aspirin group and four in the rivaroxaban-alone group.

// Race was reported by the patient

FIG. 2A and FIG. 2B together are Table 2, which shows the efficacy outcomes for the COMPASS clinical trial. The legend for FIGS. 2A and 2B is as follows:

* ALI denotes acute limb ischemia, CHD coronary heart disease, CI confidence interval, and CV cardiovascular.

† Only P values for the primary outcome are confirmatory.

δ There was no adjustment for the testing of these outcomes.

¶ One participant in the rivaroxaban-alone group had more than one type of stroke.

A total of 26 of the 392 participants who were reported to have atrial fibrillation had a stroke: 7 participants in the rivaroxaban-plus-aspirin group, 8 participants in the rivaroxaban-alone group, and 11 participants in the aspirin-alone group.

FIG. 3 is a graph showing the cumulative incidence of the primary efficacy outcome of cumulative risk of cardiovascular death, stroke, or myocardial infarction between administration of rivaroxaban plus aspirin, rivaroxaban alone, or aspirin alone in the COMPASS clinical trial.

Participants in the rivaroxaban-plus-aspirin group received 2.5 mg of rivaroxaban twice daily and 100 mg of aspirin once daily. Participants in the rivaroxaban-alone group received 5 mg of rivaroxaban twice daily and an aspirin-matched placebo once daily. Participants in the aspirin-alone group received 100 mg of aspirin once daily and a rivaroxaban-matched placebo twice daily. The inset shows the same data on an expanded y axis.

FIG. 4 is a graph showing the efficacy outcome of the COMPASS clinical trial. "HR" is hazard ratio. Data above the bars show HR and 95% confidence interval versus aspirin. "BID" means twice daily; "CV" means cardiovascular; and "MI" means myocardial infarction.

FIG. 5A and FIG. 5B together are Table 3, which shows the incidence of bleeding events and the net clinical benefit in the COMPASS clinical trial. The legend for the figure is as follows:

\* ICH denotes intracranial hemorrhage, and ISTH International Society on Thrombosis and Haemostasis.

† If a participant had more than one event of major bleeding, only the most serious bleeding event was counted in these analyses.

FIG. 6 is a graph showing safety data from the COMPASS clinical trial in terms of major bleeding and sites of major bleeding. Data above the bars show HR and 95% confidence interval versus aspirin. Abbreviations are as with other figures. "OD" means once daily.

FIG. 7A and FIG. 7B show data and a graphic representation of the hazard ratio for cardiovascular death, stroke, or myocardial infarction by subgroup of participants for rivaroxaban plus aspirin and aspirin alone in the COMPASS clinical trial.

The size of each box is proportional to the number of events. Arrows indicate that the limits of the confidence interval are not shown. The subgroup labeled "Western Europe" also includes participants in Israel, Australia, and South Africa. GFR denotes glomerular filtration rate.

FIG. 9 is a graph showing individual limb-specific outcomes in the PAD cohort of the COMPASS clinical trial.

DETAILED DESCRIPTION OF THE INVENTION

Figure 3:
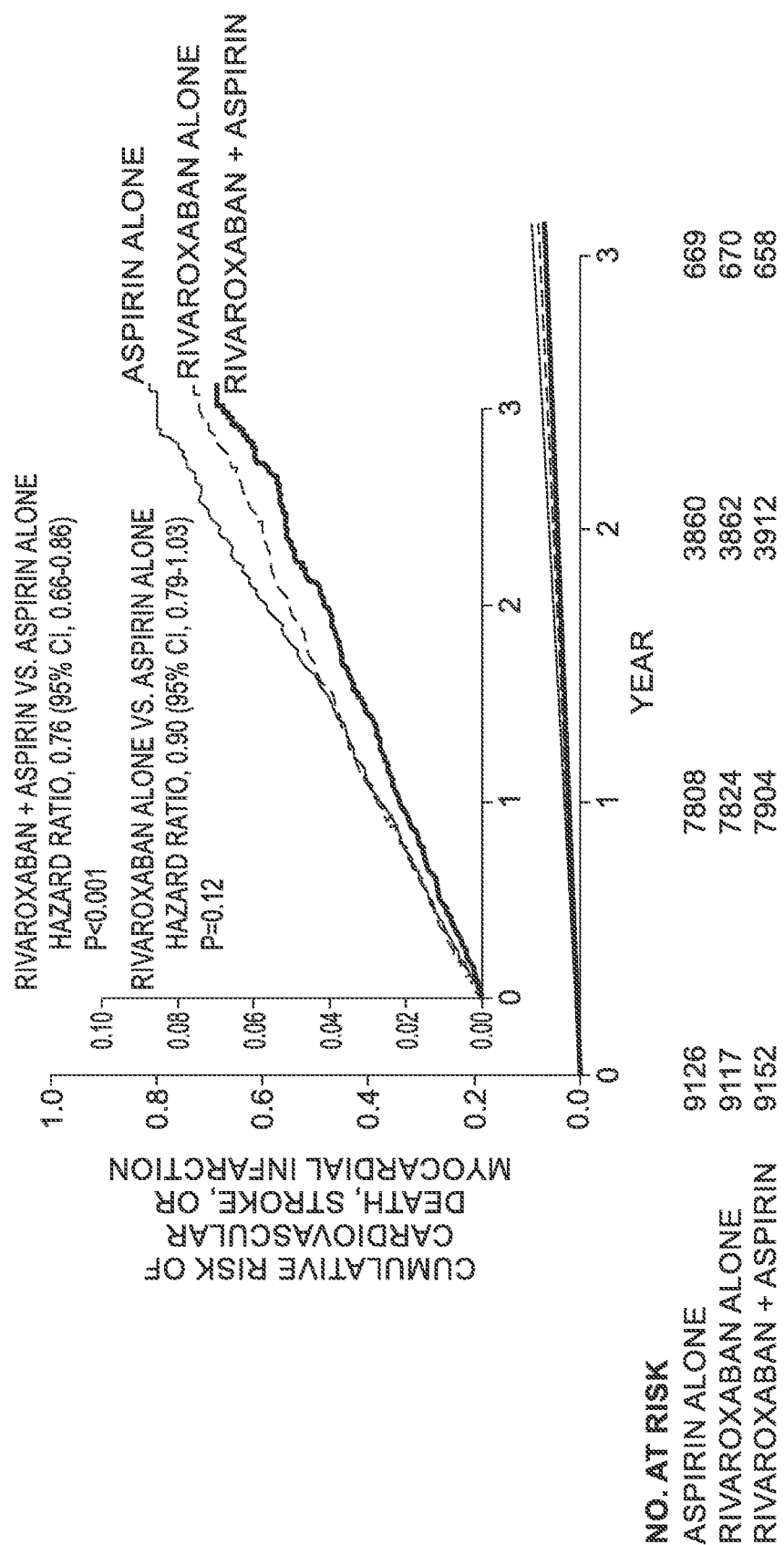

A 2.5 mg dose twice daily of rivaroxaban administered in combination with aspirin has been shown to be more effective than aspirin alone in reducing major adverse cardiovascular events including myocardial infarction, stroke and cardiovascular death in patients with stable atherosclerotic vascular disease, including patients with CAD and/or PAD, with an acceptable safety profile. In patients with PAD, a 2.5 mg dose twice daily of rivaroxaban administered in combination with aspirin reduced the number of major adverse limb events such as acute limb ischemia or amputation.

Major adverse limb events ("MALE") as used herein is defined as the development of acute limb ischemia or chronic limb ischemia including major amputations not included in acute limb ischemia or chromic limb ischemia. Major adverse cardiovascular events are abbreviated as MACE.

Rivaroxaban may be prepared as described in WO 01/47919, and is commercially available. Aspirin is also known as acetylsalicylic acid or "ASA."

Dosages to be used in embodiments of the present invention include rivaroxaban at 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.5, or 3.5 mg administered twice daily in combination with aspirin. In another embodiment rivaroxaban is administered at a dosage of 1.8-3.0, 1.9-2.9, 2.0-2.8, 2.1-2.7, 2.2-2.6, 2.3-2.5, 2.4-2.8, 2.4-2.9, 2.4-2.7, 2.4-3.0, 2.3-2.6, 2.4-2.6, about 2.5, or 2.5 mg twice daily in combination with aspirin. Aspirin may be administered at 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 115, 120, 125, 130, 135, 140, 145, or 150 mg once daily in combination with twice daily rivaroxaban. Aspirin may also be administered in the combination therapy at 30-200, 30-190, 30-180, 30-170, 30-160, 30-150, 40-140, 50-130, 60-120, 70-150, 70-140, 70-130, 70-120, 70-110, 70-100, 70-90, 70-80, 75-150, 75-140, 75-130, 75-120, 75-110, 75-100, 75-90, 75-85, about 75, 75, 80-150, 80-120, 80-100, 90-150, 90-140, 90-130, 90-120, 90-110, 90-100, 100-200, 100-190, 100-180, 100-170, 100-160, 100-150, 100-140, 100-130, 100-120, 100-110, about 100, or 100 mg once daily. In another embodiment, the twice daily rivaroxaban dosage is in combination with aspirin administered twice daily, with each of the twice daily aspirin dosages being 20, 25, 30, 35, 36, 37, 38, 39, 40, 41, 42, 43, 44, 45, 46, 47, 48, 49, 50, 51, 52, 53, 54, 55, 60, 65, 70, or 75 mg aspirin. In one embodiment, rivaroxaban is administered at 2.5 mg twice daily and aspirin is administered at 75-100 mg once daily. In certain embodiments rivaroxaban is administered at 2.5 mg twice daily and aspirin is administered at 75, 81 or 100 mg once daily. It is believed that chronic administration of aspirin at doses between 75 mg to 100 mg are comparable based on the pharmacokinetic profiles, pharmacodynamic effects and results of clinical studies and meta-analyses of aspirin at these dosages.

In a further embodiment rivaroxaban is administered at 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.5, or 3.5 mg in combination with aspirin. In another embodiment rivaroxaban is administered at a dosage of 1.8-3.0, 1.9-2.9, 2.0-2.8, 2.1-2.7, 2.2-2.6, 2.3-2.5, 2.4-2.8, 2.4-2.9, 2.4-2.7, 2.4-3.0, 2.3-2.6, 2.4-2.6, about 2.5, or 2.5 mg in combination with aspirin. Aspirin may be administered at 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 115, 120, 125, 130, 135, 140, 145, or 150 mg in combination with rivaroxaban. Aspirin may also be administered in the combination therapy at 30-200, 30-190, 30-180, 30-170, 30-160, 30-150, 40-140, 50-130, 60-120, 70-150, 70-140, 70-130, 70-120, 70-110, 70-100, 70-90, 70-80, 75-150, 75-140, 75-130, 75-120, 75-110, 75-100, 75-90, 75-85, about 75, 75, 80-150, 80-120, 80-100, 90-150, 90-140, 90-130, 90-120, 90-110, 90-100, 100-200, 100-190, 100-180, 100-170, 100-160, 100-150, 100-140, 100-130, 100-120, 100-110, about 100, or 100 mg. In one embodiment, rivaroxaban is administered at 2.5 mg and aspirin is administered at 75-100 mg. In certain embodiments rivaroxaban is administered at 2.5 mg and aspirin is administered at 75, 81 or 100 mg.

The combination therapy may be administered using separate dosage forms for rivaroxaban and aspirin, or using a combination dosage form containing both rivaroxaban and aspirin. A combination dosage form further comprises a pharmaceutically acceptable excipient. If a combination dosage form is used, the invention includes using a combination dosage form for one of the daily administrations and using a dosage form containing rivaroxaban without aspirin as the second dosage form in the daily regimen. The invention also includes using a combination dosage form containing aspirin and rivaroxaban for both of the twice daily administrations. "Combinations" mean for the purposes of the invention not only dosage forms which comprise all the components (so-called fixed dose combinations), and combination packs or kits which comprise the components separate from one another in a package together, optionally with instructions for use according to one of the methods of treatment or methods of reducing the risk of a disorder or injury disclosed herein, but also components administered simultaneously or sequentially as long as they are employed for the prophylaxis and/or treatment of the same disease. The combinations of the invention may also be used in the manufacture of a medicament.

The individual active ingredients of the combinations are disclosed in the literature and are commercially available. They can be employed in doses that, if used alone without the other elements of the claimed combination, are subtherapeutically effective doses.

Formulations of rivaroxaban are known in the art and include the formulations disclosed in U.S. Pat. No. 7,157,456 to Straub et al., issued Jan. 2, 2007 and in U.S. Pat. No. 9,402,851 to Benke, issued Aug. 2, 2016. Combination dosage forms comprising both rivaroxaban and aspirin can be made by following these examples for formulations of rivaroxaban, well-known formulations of aspirin, and the understanding of the person of ordinary skill in pharmaceutical formulation.

The methods and combinations disclosed herein may be used in combination with a further cardiovascular medication or medications. For example, the methods and combinations involving rivaroxaban and aspirin disclosed herein may be used with one or more of the following further cardiovascular medications: (1) angiotensin-converting enzyme (ACE) inhibitors, such as benazepril (Lotensin®), captopril (Capote®), enalapril (Vasotec®), fosinopril (Monopril®), lisinopril (Prinivil®, Zestril®), moexipril (Univasc®), perindopril (Aceon®), quinapril (Accupril®), ramipril (Altace®), and trandolapril (Mavik®); (2) angiotensin II (AII) receptor antagonists, such as embusartan, losartan (Cozaar®), valsartan (Diovan®), irbesartan (Avapro®), candesartan (Atacand®), eprosartan (Teveten®) and telmisartan (Micardis®); (3) statins, such as atorvastatin (Lipitor®), rosuvastatin (Crestor®), and simvastatin (Zocor® and FloLipid®); (4) nicotinic acids, such as lovastatin (Advicor®), (5) cholesterol absorption inhibitors such as ezetimibe/simvastatin (Vytorin®); and (6) beta-adrenergic blocking agents such as acebutolol (Sectral®), atenolol (Tenormin®), betaxolol (Kerlone®), bisoprolol/hydrochlorothiazide (Ziac®), bisoprolol (Zebeta®), metoprolol (Lopressor®, Toprol® XL), nadolol (Corgard®), propranolol (Inderal®), and sotalol (Betapace®).

All usual administration forms are suitable for administering the combinations of the invention. Administration preferably takes place orally, lingually, sublingually, buccally, rectally, topically or parenterally (i.e. avoiding the intestinal tract, i.e. intravenous, intracardiac, intracutaneous, subcutaneous, transdermal, intraperitoneal or intramuscular), preferably orally for both rivaroxaban and aspirin.

The present invention includes pharmaceutical preparations which, besides non-toxic, inert pharmaceutically suitable excipients and/or carriers, comprise rivaroxaban, aspirin, or both rivaroxaban and aspirin and processes for producing these preparations.

The abovementioned pharmaceutical preparations may, besides the combinations of the invention, also comprise further active pharmaceutical ingredients such as the cardiovascular medications discussed herein for use with the combinations and methods of use of the present invention.

The methods and products of the invention concern dosages that are clinically proven safe and effective. Adverse events that impact whether the inventive combinations and combination therapy are safe are adverse bleeding events that include, for example, major bleeding, minor bleeding, intracranial bleeding, and symptomatic bleeding into a critical organ. "Major bleeding" as used herein is a modification of the International Society on Thrombosis and Haemostasis (ISTH) criteria for major bleeding and includes fatal bleeding, symptomatic bleeding into a critical organ, bleeding into a surgical site requiring reoperation, and bleeding that led to hospitalization (including presentation to an acute care facility without an overnight stay). Unlike the ISTH criteria, all bleeding that led to presentation to an acute care facility or hospitalization is considered as major. In one embodiment, the term "safe" refers to a dosage determined by the US Food and Drug Administration ("US FDA") as acceptable for administration to reduce the risk of major cardiovascular events (cardiovascular death, myocardial infarction, or stroke), such as a dosage shown in trials of over 9,000 CAD and/or PAD patients taking rivaroxaban and aspirin as being safe that had serious adverse bleeding events in less than about 8.0% or in about 7.9% or in 7.9% of patients, as compared to serious adverse bleeding events in about 7.0-7.5% or in 7.3% of patients taking aspirin alone. In an embodiment directed to reducing the risk of acute limb ischemia and/or MALE in patients with PAD, the term "safe" refers to a dosage determined by the US FDA as acceptable for administration to reduce the risk of acute limb ischemia and/or MALE, such as a dosage shown in trials of over 6,000 patients taking rivaroxaban and aspirin as being safe that had serious adverse bleeding events in less than about 3.0% or in about 3.0% or in 3.0% of PAD patients, as compared to serious adverse bleeding events in about 2.0-2.5% or in 2.0% of patients taking aspirin alone.

"Safe" for the methods disclosed herein may also be measured by the net clinical benefit of the inventive method or product compared to administration of aspirin alone. The net clinical benefit outcome consists of cardiovascular death, myocardial infarction, stroke, and fatal or critical organ bleeding.

According to the invention, the terms "effective" or "efficacy," as they relate to terms such as dose, dosage regimen, or treatment with an anticoagulant that is rivaroxaban and aspirin refer to reducing the risk of myocardial infarction, stroke, or cardiovascular death in patients with CAD and/or PAD or other atherosclerotic vascular disease, such as by reducing the risk when compared to therapy with aspirin alone. Preferably, the terms "effective" and "efficacy" refer to a dosage determined by the US FDA as acceptable for administration to reduce the risk of major cardiovascular events (cardiovascular death, myocardial infarction, or stroke) in CAD and/or PAD patients, or to reduce the risk of acute limb ischemia or MALE generally in PAD patients.

One measure of efficacy is the hazard ratio of the occurrence of stroke, myocardial infarction or cardiovascular death between the inventive method and administration of aspirin alone. For example, the terms "effective" or "efficacy" for patients with CAD and/or PAD refers to a therapy wherein the hazard ratio in patients having CAD and/or PAD for myocardial infarction, stroke, or cardiovascular death with the administration of rivaroxaban and aspirin compared to aspirin alone is 0.70-0.80, 0.60-0.80, 0.50-0.90, or 0.76, with a 95% confidence interval of at least 0.56 to 0.96 or at least 0.45 to 1.10. Optionally the hazard ratio for major bleeding events with the administration of rivaroxaban and aspirin compared to aspirin alone is 1.60-1.90 with a 95% confidence interval of at least 1.35 to 2.15. These hazard ratios may be obtained from studies in a population of at least 9,000 CAD and/or PAD patients In other embodiments, the clinical trials and the populations being treated have more than 10,000, more than 15,000, or more than 20,000 patients enrolled suffering from CAD and/or PAD that form a population from which the hazard ratios may be determined and that have a sufficiently large enrollment to establish to the satisfaction of the US FDA the safety and efficacy of the administration of rivaroxaban in combination with aspirin.

In another example, the terms "effective" or "efficacy" for patients with PAD refer to a therapy wherein the hazard ratio for patients having PAD for myocardial infarction, stroke, or cardiovascular death with the administration of rivaroxaban and aspirin compared to aspirin alone is 0.70-0.80, 0.60-0.80, 0.50-0.90, or 0.72 with a 95% confidence interval of at least 0.57 to 0.90 or at least 0.45 to 1.0.

In another embodiment concerning patients with PAD according to the invention, an "effective" dose, dosage regimen, or treatment with an anticoagulant that is rivaroxaban and aspirin refer to reducing the risk of acute limb ischemia, such as by reducing the risk when compared to therapy with aspirin alone. In this embodiment, effective therapy refers to a therapy wherein the hazard ratio for acute limb ischemia with the administration of rivaroxaban and aspirin compared to aspirin alone is 0.50-0.60, or 0.56 with a 95% confidence interval of at least 0.30 to 1.00, or 0.32 to 0.99.

In certain embodiments, the hazard ratio for major bleeding events in patients with CAD and/or PAD with the administration of rivaroxaban and aspirin compared to aspirin alone is 1.60-1.90 with a 95% confidence interval of at least 1.35 to 2.15, or is 1.84 with a 95% confidence interval of 1.50 to 2.26.

These hazard ratios may be obtained from studies in patient populations over a sufficient duration that enough events (e.g., cardiovascular outcomes such as myocardial infarction, cardiovascular death, etc.) occur to allow for statistically meaningful measurement such as would be acceptable by the US FDA. Useful studies for the hazard ratios described herein to be measured involve a population of at least 9,000 CAD and/or PAD patients over more than two years. In other embodiments, the clinical trials and the populations being treated have more than 10,000, more than 15,000, or more than 20,000 patients enrolled suffering from CAD and/or PAD that form a population from which the hazard ratios may be determined. For methods of treatment and reduction of risk in PAD, the study size may be more than 2,000, more than 3,000, more than 4,000, more than 2,400; or 2492 PAD patients over at least two years.

In one embodiment, a treatment according to the present invention is efficacious when in a study of at least 9,000 patients with stable atherosclerotic disease it is determined that the primary endpoint of cardiovascular death, stroke, or myocardial infarction occurs in 4.1% of patients or less assigned to a combination therapy of rivaroxaban twice daily and aspirin once daily when aspirin alone resulted in 5.4% of the patients having a primary endpoint. In other embodiments, a study of at least 10,000, 15,000, or 20,000 patients is used to show the achievement of primary endpoints within these numerical measurements. In an embodiment directed to patients with PAD, a treatment according to the present invention is efficacious when in a study of at least 2,400 patients with PAD it is determined that the primary endpoint of cardiovascular death, stroke, or myocardial infarction occurs in 2.8% of patients or less assigned to a combination therapy of rivaroxaban twice daily and aspirin once daily when aspirin alone resulted in 3.92% of the patients having a primary endpoint. In other embodiments, a study of at least 2,492; 5,000; or 8,000 patients is used to show the achievement of primary endpoints within these numerical measurements for PAD. In an embodiment directed to patients with PAD, a treatment according to the present invention is efficacious when in a study of at least 2,400 patients with PAD it is determined that the endpoint of acute limb ischemia occurs in 0.42% of patients or less assigned to a combination therapy of rivaroxaban twice daily and aspirin once daily when aspirin alone resulted in 0.75% of the patients having acute limb ischemia.

Alternatively, effective therapy is found according to the present invention by reducing the crude cumulative incidence of cardiovascular death, myocardial infarction and stroke by at least 1.3% when compared to therapy with aspirin alone over the same duration of time.

Because the products and methods of the present invention involve medications that cause the desired reduction in the risk of myocardial infarction, stroke, or cardiovascular death yet also cause undesired bleeding, the "net clinical benefit" of the therapy is important to consider. The "net clinical benefit" composite is a positive benefit risk ratio that was derived using severe bleeding events (intracranial bleeding, fatal bleeding, and critical organ bleeding) as a component of the composite. In clinical studies, the risk of the composite net clinical benefit outcome of cardiovascular death, stroke, myocardial infarction, fatal bleeding or symptomatic bleeding into a critical organ was lower with twice-daily 2.5 mg rivaroxaban combined with once daily 100 mg aspirin (4.7%) than with aspirin alone (100 mg once daily) (5.9%), hazard ratio 0.80.

In one embodiment, the invention concerns a safe and effective pharmaceutical product for reducing the risk of myocardial infarction, stroke or cardiovascular death in a human patient with coronary artery disease and/or peripheral artery disease, wherein the pharmaceutical product comprises 2.5 mg rivaroxaban and 75, 81, or 100 mg aspirin. In a further embodiment, the invention concerns a safe and effective pharmaceutical product for reducing the risk of myocardial infarction, stroke or cardiovascular death in a human patient with coronary artery disease and/or peripheral artery disease, wherein the pharmaceutical product comprises 2.5 mg rivaroxaban and 75-100 mg aspirin. The pharmaceutical product may also contain pharmaceutically suitable excipients, such as fillers, disintegrants, etc.

In one embodiment, the invention is directed to a method of prevention of stroke, myocardial infarction and cardiovascular death, and for the prevention of acute limb ischemia and mortality in patients with coronary artery disease (CAD) or peripheral artery disease (PAD). comprising administering 2.5 mg of rivaroxaban in combination with 75 mg-100 mg of aspirin. Rivaroxaban may be administered once or twice daily in a dose of 2.5 mg. In another embodiment, the invention is a method for the prevention of atherothrombotic events in adult patients with severe coronary artery disease comprising administering a therapeutically effective amount of rivaroxaban and aspirin. In another embodiment, the invention is to a method for reducing the risk in patients with stable peripheral or carotid artery disease.

In another embodiment, the invention concerns a method of reducing the risk of death, myocardial infarction or stroke in patients with heart failure and also having significant coronary artery disease following an episode of decompensated heart failure by administering 2.5 mg rivaroxaban in combination with other medications that are the standard of care for heart failure. In one embodiment of this invention, the method comprises administering to a patient suffering from heart failure and/or coronary artery disease 2.5 mg rivaroxaban twice daily, optionally also administering standard medications known to those of ordinary skill in the art as approved for use in heart failure and coronary artery disease, such as without limitation beta blockers, ACE inhibitors, angiotensin-receptor blockers (ARBs), diuretics, etc. In one embodiment the patients suffering from heart failure and also having significant coronary artery disease also have PAD.

There is also provided a method of reducing the risk of all-cause mortality (ACM), myocardial infarction and/or stroke in a patient with heart failure and/or significant coronary artery disease comprising administering 2.5 mg of rivaroxaban, and wherein optionally the patient is also receiving other medications that are known within the standard of care. Standard care may include a diuretic, renin angiotensin system (RAS) inhibitor/vasodilator therapy (angiotensin-converting enzyme inhibitors, angiotensin receptor blockers or hydralazine/nitrates), beta blocker therapy, aldosterone antagonist if indicated, and aspirin (or other antiplatelet agent as appropriate). The dose of aspirin should be 100 mg or less per day, unless not clinically appropriate. Dual antiplatelet therapy is allowed where indicated.

Examples

Trial Conduct

The COMPASS trial, conducted at 602 centers in 33 countries, is a double-blind, double-dummy, randomized trial using a 3-by-2 partial factorial design and involving patients with a history of stable atherosclerotic vascular disease. In one randomized comparison (now completed and reported here and in Eikelboom, supra and in Anand, "Rivaroxaban with or without aspirin in patients with stable peripheral or carotid artery disease: an international, randomized, double-blind, placebo-controlled trial," Lancet; published online at S0140-6736(17)32409-1 on Nov. 10, 2017)), rivaroxaban with or without aspirin was compared with aspirin alone.

The trial protocol was approved by the relevant health authorities (including the US FDA) and institutional review boards.

Eligibility

Patients were eligible if they provided written informed consent and met the criteria for coronary artery disease, peripheral arterial disease, or both. Patients with coronary artery disease who were younger than 65 years of age were also required to have documentation of atherosclerosis involving at least two vascular beds or to have at least two additional risk factors (current smoking, diabetes mellitus, an estimated glomerular filtration rate ("GFR")<60 ml per minute, heart failure, or nonlacunar ischemic stroke≥1 month earlier). Exclusion criteria were a high bleeding risk; a recent stroke or previous hemorrhagic or lacunar stroke; severe heart failure; advanced stable kidney disease (estimated GFR<15 ml per minute); the use of dual antiplatelet therapy, anticoagulation, or other antithrombotic therapy; and noncardiovascular conditions deemed by the investigator to be associated with a poor prognosis.

Randomization and Follow-Up

Eligible participants (except those who underwent randomization 4 to 14 days after coronary-artery bypass graft ("CABG") surgery) entered a run-in phase during which they received a rivaroxaban-matched placebo twice daily and aspirin at a dose of 100 mg once daily. The purpose of the run-in phase was to identify participants who were unwilling or unable to adhere to the trial regimen, who had adverse events, or who were otherwise not suitable for randomization. Patients who underwent randomization 4 to 14 days after CABG surgery were not required to participate in the run-in phase because thrombotic graft occlusion is most common during the first few weeks after surgery and we sought to enroll such patients promptly.

Participants who adhered to the assigned regimen and who did not have adverse events, as well as those enrolled 4 to 14 days after CABG surgery, were randomly assigned in a 1:1:1 ratio to receive rivaroxaban (2.5 mg twice daily) plus aspirin (100 mg once daily), rivaroxaban (5 mg twice daily) with an aspirin-matched placebo once daily, or aspirin (100 mg once daily) with a rivaroxaban-matched placebo twice daily, stratified according to center and the use of proton-pump inhibitor therapy at the time of randomization. Study aspirin was enteric-coated. After randomization, participants were seen at 1 and 6 months and then at 6-month intervals.

Outcomes

The primary efficacy outcome for the randomized comparison of rivaroxaban with or without aspirin versus aspirin alone was the composite of cardiovascular death, stroke, or myocardial infarction. The main safety outcome was a modification of the ISTH criteria for major bleeding and included fatal bleeding, symptomatic bleeding into a critical organ, bleeding into a surgical site requiring reoperation, and bleeding that led to hospitalization (including presentation to an acute care facility without an overnight stay). Unlike the ISTH criteria, all bleeding that led to presentation to an acute care facility or hospitalization was considered as major.

Three secondary efficacy outcomes were specified: the composite of ischemic stroke, myocardial infarction, acute limb ischemia, or death from coronary heart disease; the composite of ischemic stroke, myocardial infarction, acute limb ischemia, or cardiovascular death; and death from any cause. Tertiary efficacy outcomes included individual components of the primary and secondary outcomes, as well as hospitalization for cardiovascular causes, revascularization, limb amputation, stent thrombosis, angina, heart failure, venous thromboembolism, resuscitated cardiac arrest, and a new diagnosis of cancer. The net-clinical-benefit outcome was the composite of cardiovascular death, stroke, myocardial infarction, fatal bleeding, or symptomatic bleeding into a critical organ.

Statistical Analysis

The clinical study organizers projecting enrolling about 21,000 patients, but due to lower than expected event rates, the projected enrollment was increased to 27,400 participants. As an event-driven trial, with an expected control-group event rate of 3.3 per 100 person-years, it was designed to continue until at least 2200 participants had a confirmed primary efficacy outcome, thereby providing 90% power to detect a 20% lower risk in each of the two comparisons of rivaroxaban versus aspirin.

An independent data and safety monitoring board monitored the study, with formal stopping guidelines for efficacy and nonformal guidelines for safety. Two formal interim analyses of efficacy were planned, when 50% and 75% of primary efficacy events had occurred. A modified Haybittle-Peto rule was used, which required a difference of 4 standard deviation ("SD") at the first interim analysis that was consistent over a period of 3 months, and a consistent difference of 3 SD at the second interim analysis.

All the outcome events in all randomly assigned patients that occurred between randomization and the date of stopping the trial were included in the analysis, according to the intention-to-treat principle. An early stop of both antithrombotic treatment groups for efficacy had not been anticipated, and therefore a strategy for formal testing of secondary outcomes at the interim analysis was not prespecified.

Kaplan-Meier estimates of the cumulative risk were used to evaluate the timing of event occurrences in the three antithrombotic treatment groups. Hazard ratios and corresponding 95% confidence intervals were obtained from stratified Cox proportional-hazards models. The assumptions of the Cox models were verified with plots of log of negative log of the survival function against the log of time. All reported P values are two-sided.

Results

Participants

From March 2013 through May 2016, a total of 27,395 persons who successfully completed the run-in phase or who were enrolled 4 to 14 days after CABG surgery were randomly assigned to rivaroxaban plus aspirin, rivaroxaban, or aspirin.

Baseline characteristics are presented in FIG. 1, Table 1. The mean age of participants was 68.2 years, and 22.0% were women. Lipid-lowering agents were used by 89.8%, and angiotensin-converting-enzyme inhibitors or angiotensin-receptor blockers by 71.2%. The mean systolic blood pressure was 136 mm Hg, the mean diastolic blood pressure 78 mm Hg, and the mean total cholesterol level 4.2 mmol per liter (162 mg per deciliter). A total of 90.6% of the participants had a history of coronary artery disease, and 27.3% had a history of peripheral arterial disease.

Early Termination, Follow-Up, and Adherence

At the first formal interim analysis for efficacy (50% of planned events), the independent data and safety monitoring board recommended early termination of the randomized comparison of rivaroxaban with or without aspirin versus aspirin alone on Feb. 6, 2017, having observed a consistent difference in the primary efficacy outcome in favor of rivaroxaban plus aspirin ($z=-4.592$).

The z statistic for the comparison of rivaroxaban plus aspirin versus aspirin alone was larger than the prespecified 4 SD, but the z statistic for the comparison of rivaroxaban alone versus aspirin alone had not met this criterion ($z=-2.44$). Because there was a statistically significant effect for both comparisons, the data and safety monitoring board recommended stopping the rivaroxaban and aspirin groups of the trial.

Vital status was available for 27,331 participants (99.8%) to Feb. 6, 2017, and the mean duration of follow-up of these participants was 23 months (maximum duration, 47 months). At the final visit for this component of the trial, the percentage of participants who had permanently discontinued study treatment was 16.5% in the rivaroxaban-plus-aspirin group, 17.0% in the rivaroxaban-alone group, and 15.7% in the aspirin-alone group.

Primary Efficacy Outcome

A primary outcome event of cardiovascular death, stroke, or myocardial infarction occurred in 379 patients (4.1%) who were assigned to rivaroxaban plus aspirin, 448 (4.9%) who were assigned to rivaroxaban alone, and 496 (5.4%) who were assigned to aspirin alone (FIG. 2, showing Table 2 and FIG. 3). For the comparison of rivaroxaban (2.5 mg twice daily) plus aspirin with aspirin alone, the hazard ratio for the primary outcome was 0.76 (95% confidence interval [CI], 0.66 to 0.86; P<0.001; $z=-4.126$). For the comparison of rivaroxaban (5 mg twice daily) alone with aspirin alone, the hazard ratio was 0.90 (95% CI, 0.79 to 1.03; P=0.12; $z=-1.575$).

Figure 4:
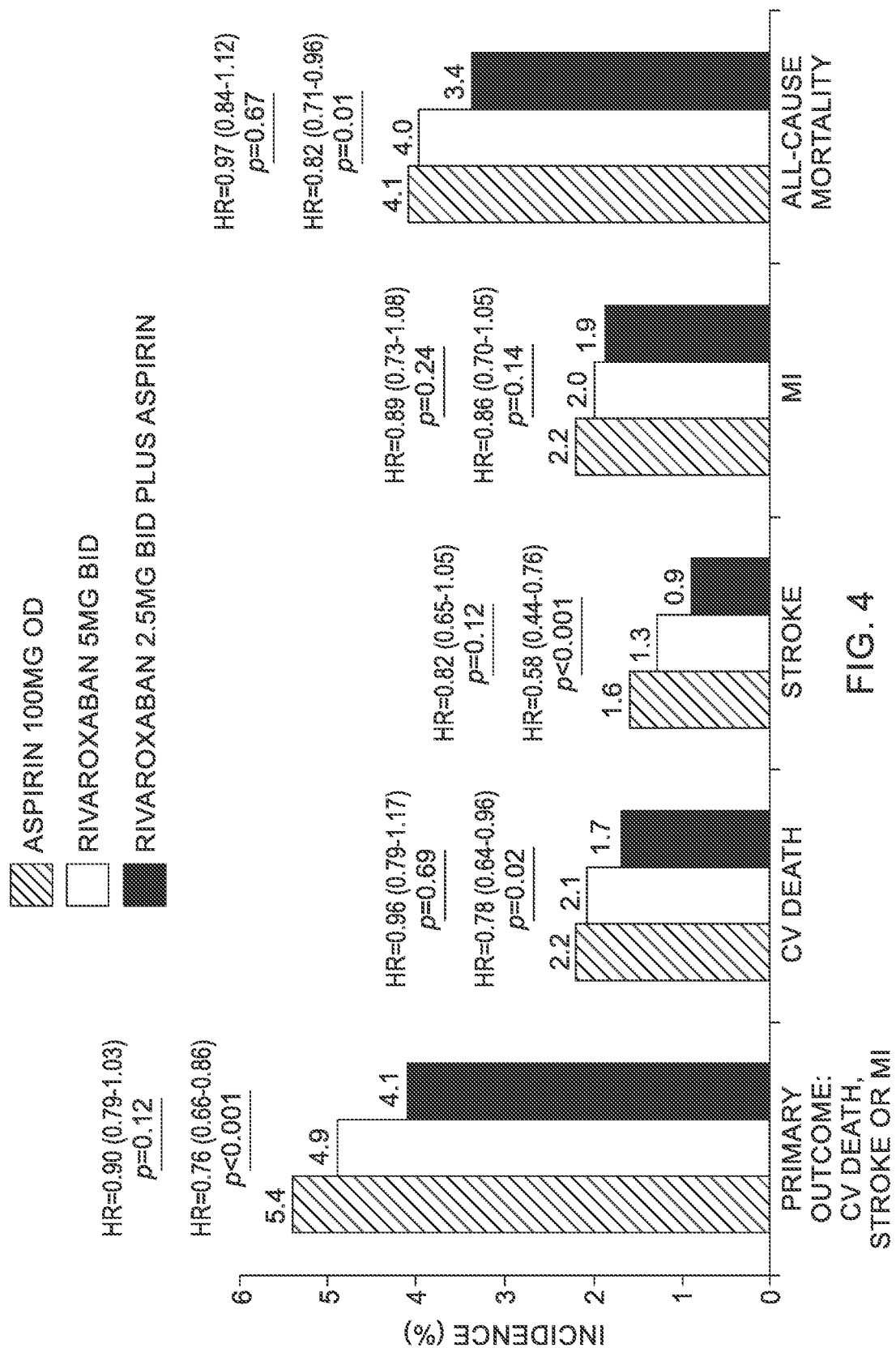

Dual pathway inhibition with rivaroxaban 2.5 mg bid plus aspirin significantly reduced the composite of cardiovascular death, stroke, and myocardial infarction by 24% (p<0.001) (FIG. 3). Rivaroxaban 2.5 mg bid plus aspirin was associated with an 18% reduction in all-cause mortality compared with aspirin alone (P=0.01)(FIG. 4). FIG. 4 also shows the efficacy outcome for each of the primary endpoints of cardiovascular death, stroke, or myocardial infarction. Rivaroxaban 5 mg bid was not associated with a significant reduction in the rate of the primary outcome compared with aspirin alone.

Secondary Efficacy Outcomes

The secondary composite outcome of ischemic stroke, myocardial infarction, acute limb ischemia, or death from coronary heart disease occurred in fewer patients in the rivaroxaban-plus-aspirin group than in the aspirin-alone group (329 patients [3.6%] vs. 450 patients [4.9%]; hazard ratio, 0.72; 95% CI, 0.63 to 0.83; P<0.001) (FIG. 2, Table 2). The secondary outcome of ischemic stroke, myocardial infarction, acute limb ischemia, or cardiovascular death also occurred in fewer patients in the rivaroxaban-plus-aspirin group than in the aspirin-alone group (389 patients [4.3%] vs. 516 patients [5.7%]; hazard ratio, 0.74; 95% CI, 0.65 to 0.85; P<0.001). There were 313 deaths (3.4%) in the rivaroxaban-plus-aspirin group as compared with 378 (4.1%) in the aspirin-alone group (hazard ratio, 0.82; 95% CI, 0.71 to 0.96; P=0.01). The threshold P value using the Hochberg procedure for each of the above comparisons was 0.0025. For the regimen of rivaroxaban alone as compared with aspirin alone, because no significant effect was seen for the primary composite outcome, formal testing of the secondary outcomes was not performed.

Bleeding and Other Adverse Events

Figure 6:
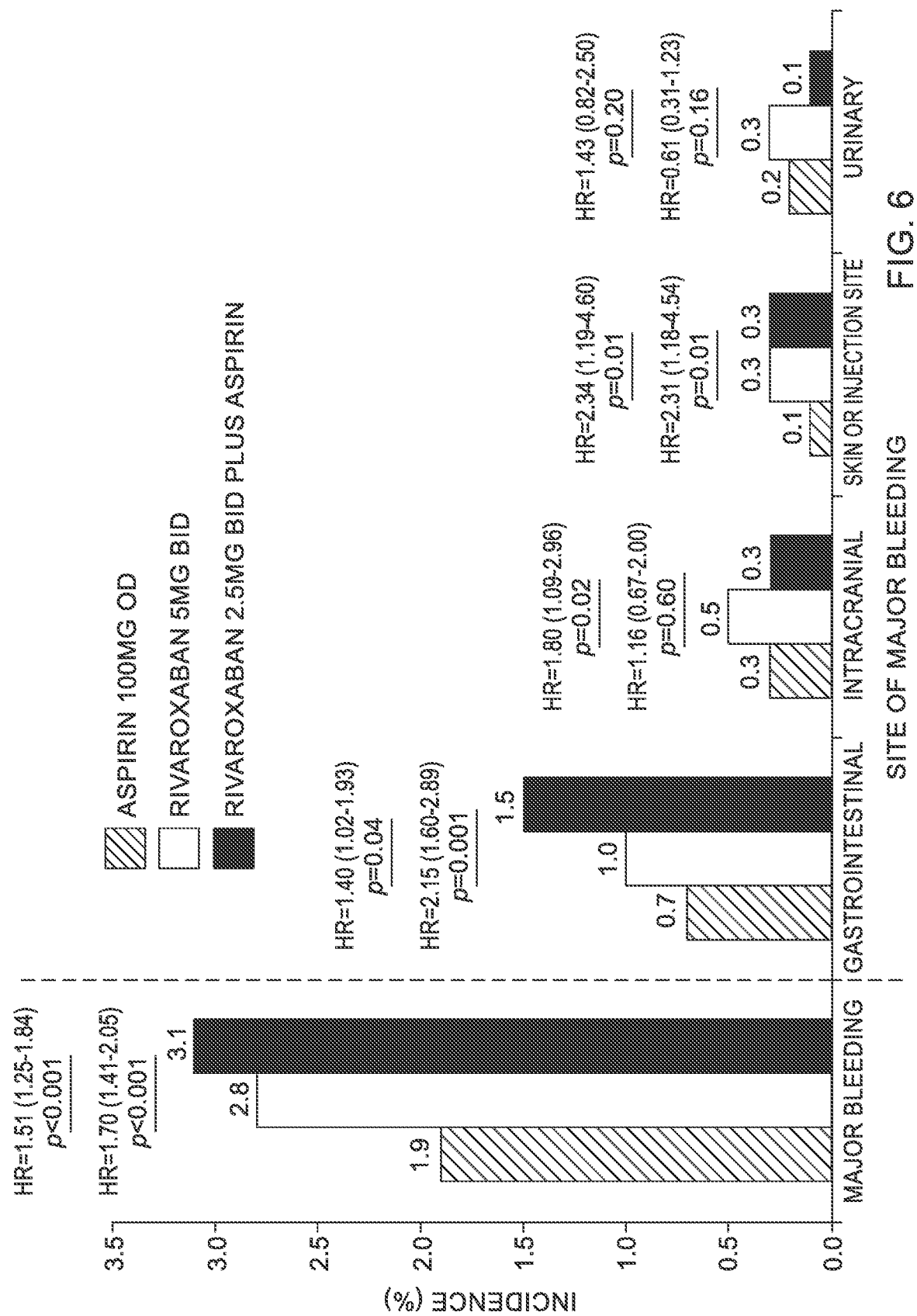

Major bleeding events occurred in more patients in the rivaroxaban-plus-aspirin group than in the aspirin-alone group (288 patients [3.1%] vs. 170 patients [1.9%]; hazard ratio, 1.70; 95% CI, 1.40 to 2.05; P<0.001) (FIG. 5, Table 3), mainly owing to a difference in bleeding that led to presentation to an acute care facility or hospitalization. Most of the excess major bleeding was into the gastrointestinal tract, with no significant between-group difference in the rate of fatal bleeding, intracranial bleeding, or symptomatic bleeding into a critical organ. FIG. 6 is a graph showing for each patient group the safety outcomes in major bleeding and sites of major bleeding. The rate of major bleeding as defined by the ISTH criteria (the composite of fatal bleeding, bleeding into a critical organ, bleeding requiring ≥2 units of transfusion within 48 hours, and bleeding associated with a decrease in the hemoglobin level of ≥2 g per deciliter) was significantly greater with rivaroxaban plus aspirin than with aspirin alone.

Major bleeding events occurred in more patients in the rivaroxaban-alone group than in the aspirin-alone group (255 patients [2.8%] vs. 170 patients [1.9%]; hazard ratio, 1.51; 95% CI, 1.25 to 1.84; P<0.001) (FIG. 5, Table 3). The excess major bleeding included symptomatic bleeding into a critical organ and bleeding that led to hospitalization.

Serious adverse events were reported in 721 patients (7.9%) assigned to rivaroxaban plus aspirin, 702 (7.7%) assigned to rivaroxaban alone, and 662 (7.3%) assigned to aspirin alone.

Net Clinical Benefit

The risk of the composite net-clinical-benefit outcome of cardiovascular death, stroke, myocardial infarction, fatal bleeding, or symptomatic bleeding into a critical organ was lower with rivaroxaban plus aspirin than with aspirin alone (431 patients [4.7%] vs. 534 patients [5.9%]; hazard ratio, 0.80; 95% CI, 0.70 to 0.91; P<0.001) (FIG. 5, Table 3). The risk of the net-clinical-benefit outcome was not significantly lower with rivaroxaban alone than with aspirin alone.

Subgroup Analyses

Figure 7A:
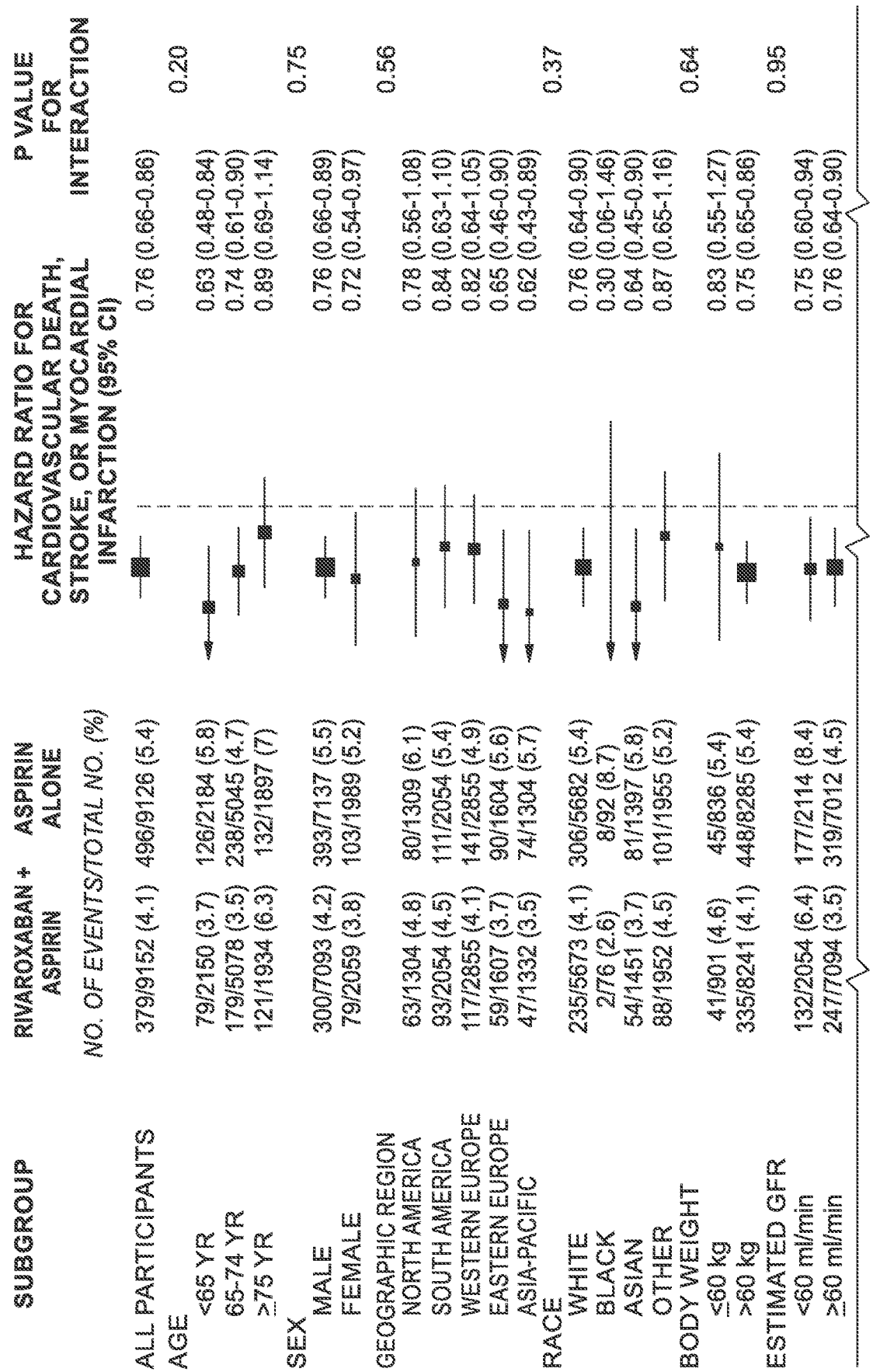
Figure 7B:
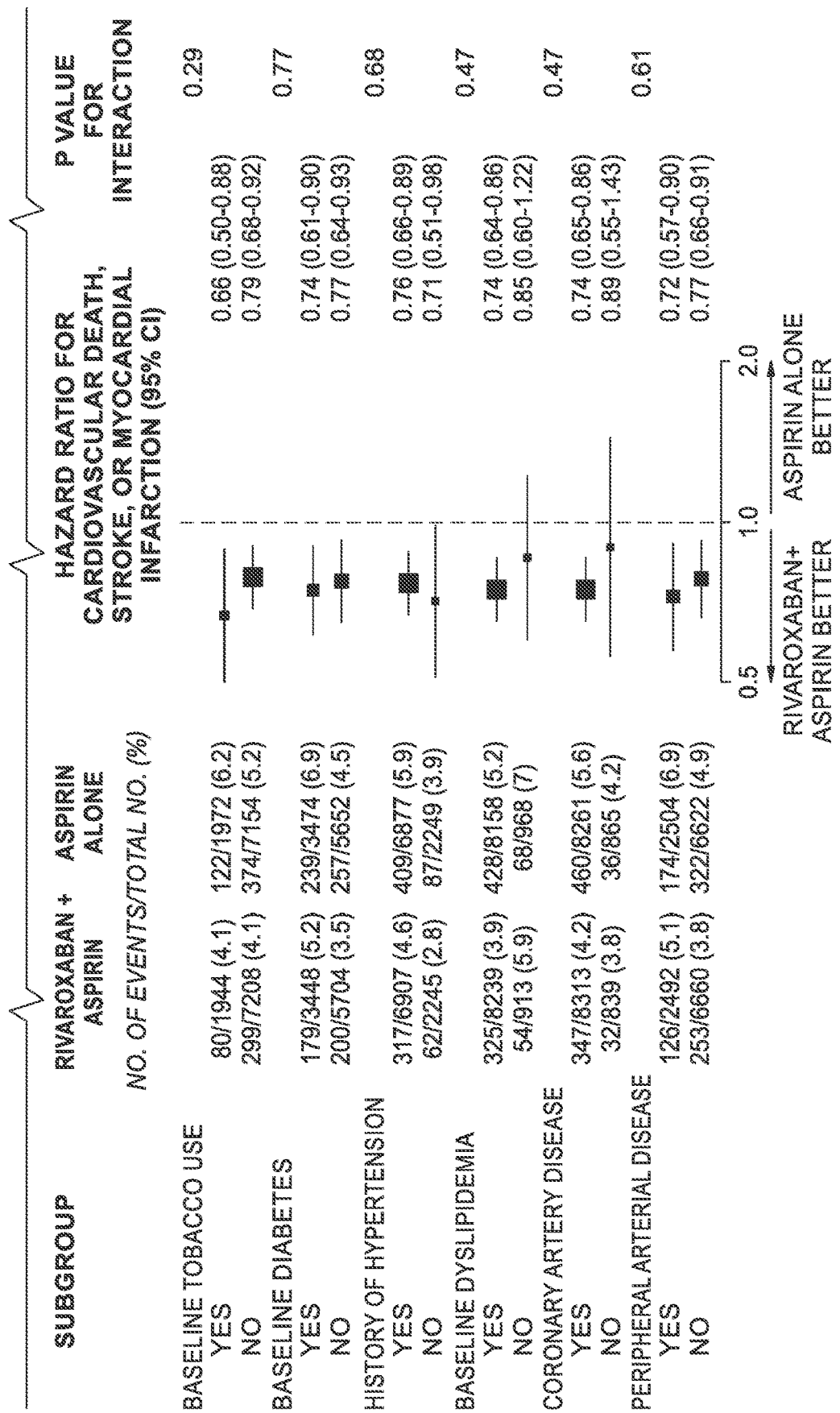

The effects of rivaroxaban plus aspirin as compared with aspirin alone on the primary outcome (FIG. 7) and on major bleeding were consistent among subgroups that were defined according to age, sex, geographic region, race or ethnic group, body weight, renal function, and history of cardiovascular risk factors (tobacco use, hypertension, diabetes, or dyslipidemia). Results in participants who met the eligibility criteria for coronary artery disease and in those who met the eligibility criteria for peripheral arterial disease were also consistent.

PAD Patients

Figure 8:
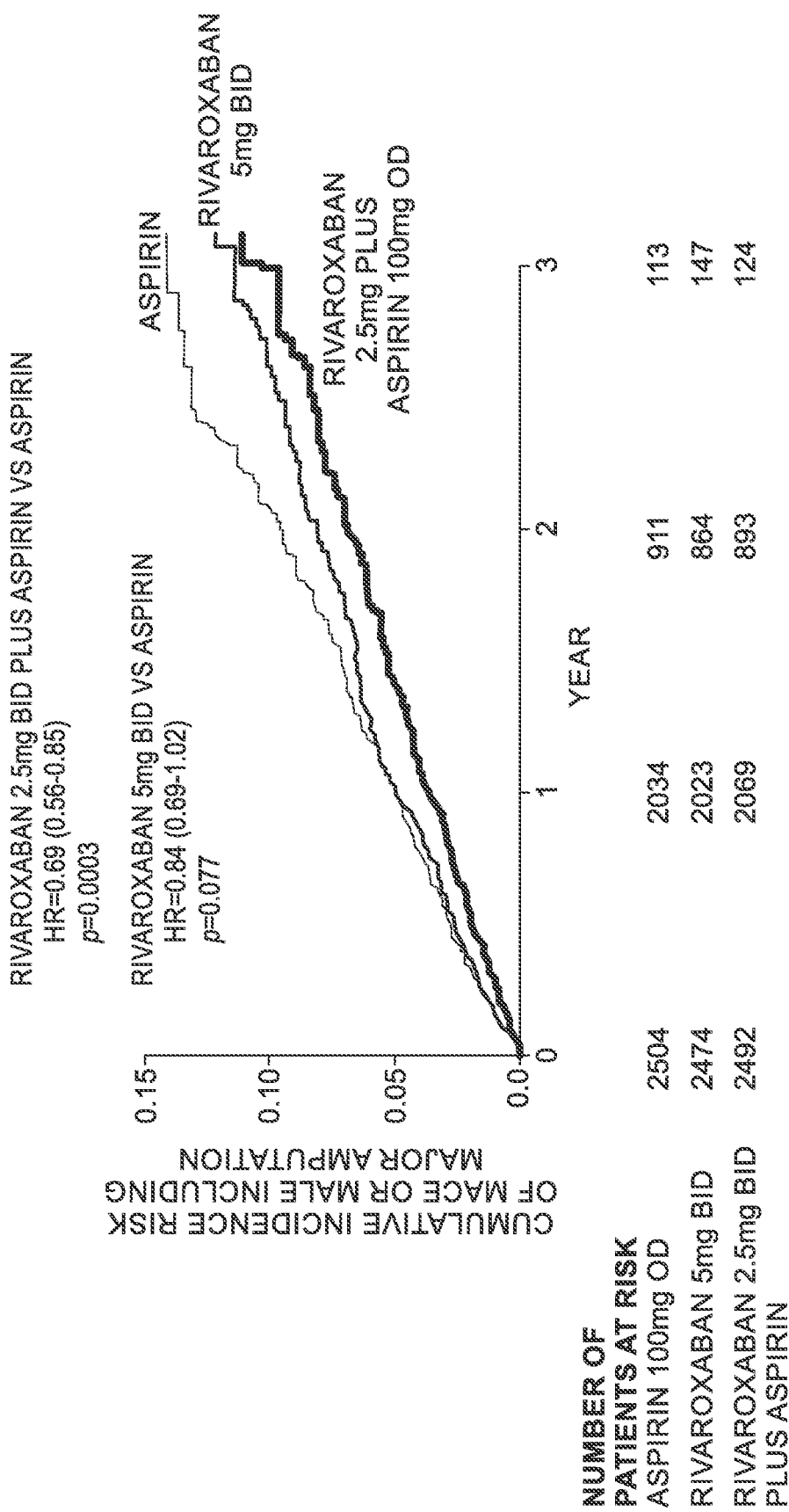
FIG. 8 is a graph showing cumulative incidence of MACE or MALE including major amputation in the PAD cohort of the COMPASS clinical trial. Abbreviations are as discussed for other figures.

In the PAD cohort of the COMPASS trial, compared with aspirin alone, dual pathway inhibition with rivaroxaban 2.5 mg bid plus aspirin significantly reduced the risk of cardiovascular death, myocardial infarction, or stroke by 28% (hazard ratio=0.54; 95% confidence interval 0.35-0.84; p=0.0054). MALE, including major amputations not included in acute limb ischemia and chromic limb ischemia, was reduced by 46% (hazard ratio=0.54; 95% confidence interval 0.35-0.82; p=0.0037). MACE, MALE or major amputation was reduced by 31% (FIG. 8). In this PAD cohort, other limb-specific outcomes, including a reduction in the risk of major amputation was reduced by 70% (FIG. 9).

Discussion

Among patients with stable atherosclerotic vascular disease, a high proportion of whom were receiving proven secondary prevention therapies, the rate of the primary outcome (a composite of cardiovascular death, stroke, or myocardial infarction) was lower by 24% with rivaroxaban (2.5 mg twice daily) plus aspirin than with aspirin alone (4.1% vs. 5.4%), but the rate of major bleeding was higher by 70% (3.1% vs. 1.9%). The rate of the net-clinical-benefit outcome was lower by 20% with rivaroxaban plus aspirin than with aspirin alone (4.7% vs. 5.9%). The comparison of rivaroxaban (5 mg twice daily) alone with aspirin alone did not show a significant difference in the primary outcome or the net-clinical-benefit outcome, but the rate of major bleeding was higher with rivaroxaban alone.

The definition of major bleeding in the COMPASS trial was based on the ISTH definition, which includes fatal bleeding, symptomatic bleeding into a critical area or organ, bleeding causing a decrease in the hemoglobin level of 2 g or more per deciliter, or bleeding that led to transfusion of 2 or more units of whole blood or red cells. However, the definition used in the COMPASS trial, which had been adopted in response to a request from regulators, differed from the ISTH definition in that it did not take into account whether bleeding was associated with a decrease in the hemoglobin level or with blood transfusion, and it included any bleeding that led to hospitalization with or without an overnight stay, thus including events that would not be considered major bleeding in other trials. Although there was also a significant increase in the rate of major bleeding with rivaroxaban with the use of the ISTH scale, there were approximately one third fewer major bleeding events with this definition than with the use of the modified ISTH definition. Our definition of net clinical benefit balanced the lower risk of cardiovascular death, stroke, or myocardial infarction against the most serious bleeding events and showed a significant benefit of combination therapy.

There are a few limitations of the trial that should be considered. First, we did not specifically study patients with a previous stroke. However, of those enrolled, 1032 also had a history of stroke, and the benefits of the combination of rivaroxaban and aspirin in preventing cardiovascular death, stroke, or myocardial infarction were consistent in these patients. Furthermore, the combination of rivaroxaban and aspirin resulted in a lower rate of ischemic stroke than aspirin alone. Second, although the majority of patients were receiving proven secondary prevention therapies, and the blood pressure and total cholesterol levels were serially recorded during the study, we did not specifically record statin use or low-density lipoprotein cholesterol levels at baseline, and the trial protocol did not specifically emphasize aggressive use of secondary prevention therapies to lower blood pressure and cholesterol levels. However, the results were consistent in patients with baseline blood pressure below or above the mean and in those with baseline cholesterol levels below or above the median, supporting the conclusion that the benefits of combination therapy are additive to those of other proven secondary preventive therapies. Third, trials that are stopped early for efficacy may overestimate the treatment effect. However, before the time of stopping, the data and safety monitoring board had observed a progressive increase in benefit of the combination of rivaroxaban and aspirin for more than 1 year. Furthermore, the data reported here include additional events that occurred before the cutoff but were not reported at the time of stopping the study and exclude some events that were refuted during adjudication. It is noteworthy that the results based on events reported by the sites and after adjudication are nearly identical.

In conclusion, in patients with stable atherosclerotic vascular disease, we compared three antiplatelet regimens: rivaroxaban (2.5 mg twice daily) plus aspirin (100 mg once daily), rivaroxaban (5 mg twice daily), and aspirin (100 mg once daily). The risk of major adverse cardiovascular events was significantly lower with the combination of rivaroxaban plus aspirin than with aspirin alone, and the risk of major bleeding was significantly higher. Rivaroxaban alone did not result in a significantly lower risk of major adverse cardiovascular events than aspirin alone and resulted in a significantly higher risk of major bleeding.

Each of the articles and patent publications discussed herein is hereby incorporated by reference in its entirety herein.

What is claimed is:

1. A method of reducing the risk of myocardial infarction, stroke or cardiovascular death in a human patient with coronary artery disease and/or peripheral artery disease, comprising administering to the human patient rivaroxaban and aspirin in amounts that are clinically proven effective in reducing the risk of myocardial infarction, stroke or cardiovascular death in a human patient with coronary artery disease and/or peripheral arterial disease, wherein rivaroxaban is administered in an amount of 2.5 mg twice daily and aspirin is administered in an amount of 75-100 mg daily.

2. The method of claim 1, wherein aspirin is administered in an amount of 100 mg daily.

3. The method of claim 1, wherein aspirin is administered in an amount of 81 mg daily.

4. The method of claim 1, wherein aspirin is administered in an amount of 75 mg daily.

5. A method of reducing the risk of myocardial infarction, stroke or cardiovascular death in a human patient with coronary artery disease and/or peripheral artery disease, the method comprising administering to the human patient rivaroxaban and aspirin in amounts that are clinically proven effective in reducing the risk of myocardial infarction, stroke or cardiovascular death in a human patient with coronary artery disease and/or peripheral arterial disease, wherein the method comprises once daily administration of a first product comprising rivaroxaban and aspirin and a second product comprising rivaroxaban, and further wherein the first product comprises 2.5 mg rivaroxaban and 75-100 mg aspirin and the second product comprises 2.5 mg rivaroxaban.

6. The method of claim 5, wherein the first product comprises 75 mg aspirin.

7. The method of claim 5, wherein the first product comprises 81 mg aspirin.

8. The method of claim 5, wherein the first product comprises 100 mg aspirin.

* * * * *

(12) SUPPLEMENTAL EXAMINATION CERTIFICATE

United States Patent  
Bruns et al.

(10) Number: US 10,828,310 F1  
(45) Certificate Issued: Feb. 10, 2021

Control No.: 96/000,348  
Filing Date: Jan. 7, 2021  
Primary Examiner: Bruce Campell No substantial new question of patentability is raised in the request for supplemental examination. See the Reasons for Substantial New Question of Patentability Determination in the file of this proceeding.

(56) Items of Information

OTHER DOCUMENTS

U.S. National Library of Medicine, ClinicalTrials.gov Archives, NCT01776424 Study Record Version 49 dated January 24, 2017, submitted with IDS on May 28, 2019 in U.S. App. 16/264032 (34 pages)

U.S. National Library of Medicine, ClinicalTrials.gov Archives, NCT01776424 History of Changes from January 25, 2013-May 7, 2019

U.S. National Library of Medicine, ClinicalTrials.gov Archives, NCT01776424 History of Changes from January 24, 2017 and May 7, 2019

U.S. National Library of Medicine, ClinicalTrials.gov Archives, NCT01776424 History of Changes from February 23, 2017 to January 24, 2018